United States Patent
Nakayama et al.

(10) Patent No.: US 10,370,473 B2
(45) Date of Patent: Aug. 6, 2019

(54) COMPOUND, CURABLE COMPOSITION, CURED PRODUCT, OPTICAL MEMBER, AND LENS

(71) Applicant: FUJIFILM Corporation, Tokyo (JP)

(72) Inventors: Takafumi Nakayama, Ashigarakami-gun (JP); Shigeki Uehira, Ashigarakami-gun (JP); Naoyuki Morooka, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 16/019,922

(22) Filed: Jun. 27, 2018

(65) Prior Publication Data

US 2018/0305486 A1    Oct. 25, 2018

Related U.S. Application Data

(63) Continuation of application No. PCT/JP2016/087132, filed on Dec. 14, 2016.

(30) Foreign Application Priority Data

Dec. 28, 2015 (JP) ................................. 2015-256829

(51) Int. Cl.
| | | |
|---|---|---|
| *C08F 220/36* | (2006.01) | |
| *C07D 221/18* | (2006.01) | |
| *C07D 241/38* | (2006.01) | |
| *C07D 471/04* | (2006.01) | |
| *C08F 2/44* | (2006.01) | |
| *G02B 1/04* | (2006.01) | |
| *C08F 220/30* | (2006.01) | |
| *C08F 216/14* | (2006.01) | |
| *C08F 220/18* | (2006.01) | |
| *C08F 220/38* | (2006.01) | |
| *C08F 222/10* | (2006.01) | |

(52) U.S. Cl.
CPC .......... *C08F 220/36* (2013.01); *C07D 221/18* (2013.01); *C07D 241/38* (2013.01); *C07D 471/04* (2013.01); *C08F 2/44* (2013.01); *C08F 220/30* (2013.01); *G02B 1/04* (2013.01); *G02B 1/041* (2013.01); *C08F 216/1416* (2013.01); *C08F 2220/185* (2013.01); *C08F 2220/1875* (2013.01); *C08F 2220/301* (2013.01); *C08F 2220/382* (2013.01); *C08F 2222/1013* (2013.01); *C08F 2800/20* (2013.01)

(58) Field of Classification Search
CPC ........................... H01L 51/0061; C08F 220/36
See application file for complete search history.

(56) References Cited

U.S. PATENT DOCUMENTS

| | | | |
|---|---|---|---|
| 6,320,020 B1 | 11/2001 | Takuma et al. | |
| 6,638,582 B1 | 10/2003 | Uchiyama et al. | |
| 9,334,352 B2 | 5/2016 | Someya et al. | |
| 2009/0143560 A1 | 6/2009 | Hatanaka et al. | |
| 2010/0044686 A1 | 2/2010 | Morishita | |
| 2010/0168444 A1 | 7/2010 | Chen et al. | |
| 2013/0105767 A1* | 5/2013 | Lin ...................... C07D 401/14 257/40 | |
| 2014/0284556 A1* | 9/2014 | Cheng ................ H01L 51/0061 257/40 | |

FOREIGN PATENT DOCUMENTS

| | | |
|---|---|---|
| CN | 101475568 A | 7/2009 |
| JP | 06-228296 A | 8/1994 |
| JP | 06-322087 A | 11/1994 |
| JP | 08-113565 A | 5/1996 |
| JP | 2000-351846 A | 12/2000 |
| JP | 4010810 B2 | 11/2007 |
| JP | 2009-126011 A | 6/2009 |
| JP | 2009-234999 A | 10/2009 |
| JP | 2009-249307 A | 10/2009 |
| JP | 2010-254806 A | 11/2010 |
| JP | 2013-64117 A | 4/2013 |
| JP | 5249781 B2 | 7/2013 |
| JP | 2014-080572 A | 5/2014 |

(Continued)

OTHER PUBLICATIONS

Ham et al. CAS: 163:45069, 2015.*
Park et al. CAS: 145:73051, 2006.*
Written Opinion issued by the International Searching Authority in International Application No. PCT/JP2017/006297, dated May 23, 2017.
International Preliminary Report on Patentability and Written Opinion issued from the International Bureau in International Application No. PCT/JP2017/006297, dated Aug. 28, 2018.

(Continued)

*Primary Examiner* — Rei Tsang Shiao
(74) *Attorney, Agent, or Firm* — Sughrue Mion, PLLC

(57) ABSTRACT

A cured product of a compound of the following formula has a low Abbe number and a high abnormal dispersibility. X and Y are O, S, N or S; Z and X—C=C—Y form 5 to 7-membered ring; $R^1$ and $R^2$ represents H, alkoxy, mercapto, thioalkoxy, amino, alkylamino, carboxy, alkylcarbonyloxy, carbamoyloxy or alkoxycarbonyloxy; and $R^3$ to $R^6$ represent substituent.

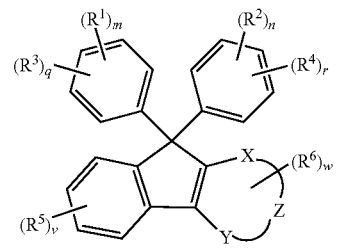

15 Claims, No Drawings

(56) References Cited

FOREIGN PATENT DOCUMENTS

| KR | 10-2017-0047977 A | | 5/2017 |
|---|---|---|---|
| WO | 2006/065105 A1 | | 6/2006 |
| WO | WO2006065105 | * | 6/2006 |
| WO | 2007/055390 A1 | | 5/2007 |
| WO | 2015/076601 A1 | | 5/2015 |

OTHER PUBLICATIONS

International Search Report, issued by International Searching Authority in International Application No. PCT/JP2017/006297, dated May 23, 2017.
R. R. Rajawinslin et al., "Iron/acetic acid mediated intermolecular tandem C—C and C—N bond formation; an easy access to acridinone and quinoline derivatives", RSC Advances, Royal Society of Chemistry, vol. 4, 2014 (pp. 37806-37811).
John E. McMurry et al., "Synthesis of isocaryophyliene by titanium-induced keto ester cyclization", Tetrahedron Letters, vol. 24, No. 18, 1983 (pp. 1885-1888).
R.E. Hughes et al., "Total Synthesis of d,l-caryophyllene and d,l-isocaryophyllene", J. Am. Chem. Soc., vol. 85, 1963 (pp. 362-363).
Frank D. Popp, "Synthesis of Potential Antineoplastic Agents. XXI. Compounds Related to Ellipticine", Journal of Heterocyclic Chemistry, vol. 9, p. 1399-1401 (Dec. 1972).
International Search Report, issued by International Searching Authority in corresponding International Application No. PCT/JP2016/087132, dated Mar. 14, 2017.
Written Opinion issued by the International Searching Authority in corresponding International Application No. PCT/JP2016/087132, dated Mar. 14, 2017.
International Preliminary Report on Patentability and Written Opinion issued from the International Bureau in counterpart International Application No. PCT/JP2016/087132, dated Jul. 3, 2018.
Office Action dated Apr. 16, 2019 issued by the Japanese Patent Office in Japanese application No. 2017-558923.

* cited by examiner

COMPOUND, CURABLE COMPOSITION, CURED PRODUCT, OPTICAL MEMBER, AND LENS

CROSS-REFERENCE TO RELATED APPLICATIONS

This application is a Continuation of PCT International Application No. PCT/JP2016/087132, filed on Dec. 14, 2016, which claims priority under 35 U.S.C. Section 119(a) to Japanese Patent Application No. 2015-256829 filed on Dec. 28, 2015. Each of the above applications is hereby expressly incorporated by reference, in its entirety, into the present application.

BACKGROUND OF THE INVENTION

1. Field of the Invention

The present invention relates to a compound, a curable composition, a cured product, an optical member, and a lens.

2. Description of the Related Art

In the related art, a glass material has been used in an optical member of an image pick-up module of a camera, a video camera, a camera-equipped cellular phone, a videophone, a camera-equipped intercom, or the like. Since a glass material has various optical properties and has excellent environmental resistance, the glass material has been preferably used but has disadvantages in that reduction in weight and size is not easy and workability and productivity are poor. In contrast, since a resin cured product may be mass-produced and has excellent workability, the resin cured product has been used in various optical members in recent years.

In recent years, along with the reduction in size of image pick-up modules, it has been required to reduce the size of the optical member used in the image pick-up module. However, in a case where the size of the optical member is reduced, a problem of chromatic aberration occurs. With respect to an optical member using a resin cured product, reducing the Abbe number by changing properties after curing by adding various additives to the curable composition, so as to correct the chromatic aberration has been researched.

As a monomer used in a curable composition for manufacturing an optical member, a compound having a fluorene skeleton is used. For example, JP2013-64117A discloses a polyester resin having a 9,9-bisarylfluorene skeleton and a molded article formed of a polyester resin. Here, it is considered that a polyester resin having both a high refractive index and low birefringence and having heat resistance may be obtained. JP2009-249307A discloses a bis(hydroxyphenyl)anthracene compound having an anthracene skeleton. JP2009-249307A also has a purpose of obtaining a raw material for an optical member having a high refractive index, low birefringence, and high heat resistance.

However, the compound having a fluorene skeleton or a structure similar to a fluorene skeleton may be used in a field other than an optical material. For example, US2010/168444A discloses a diindenothiophene derivative as a coloring agent used in a coloring agent-sensitized solar cell.

SUMMARY OF THE INVENTION

However, in a case where cured products are formed by using the compounds disclosed in JP2013-64117A and JP2009-249307A in curable compositions, the present inventors have conducted research and clearly found that Abbe numbers of the cured products are not sufficiently low, and an abnormal dispersibility tends to be low. Even in a case where the compound disclosed in US2010/168444A is applied to the curable composition, a low Abbe number or a high abnormal dispersibility of the cured product was not able to be achieved.

Therefore, in order to solve the problems in the related art, the present inventors have conducted research for the purpose of providing a compound that is able to form a cured product having a low Abbe number and a high abnormal dispersibility.

Specific means for achieving the object is as follows.

[1] A compound represented by Formula (1),

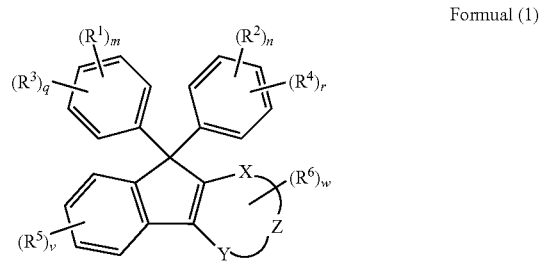

Formual (1)

in Formula (1), X and Y each independently represent an oxygen atom, a sulfur atom, a nitrogen atom, or a carbon atom, at least one of X or Y is an oxygen atom, a sulfur atom, or a nitrogen atom; and Z is an atomic group that forms a 5 to 7-membered ring together with X—C=C—Y and represents an atomic group including at least one selected from a carbon atom and a heteroatom;

$R^1$ and $R^2$ each independently represent a hydroxyl group, an alkoxy group having 2 to 6 carbon atoms that may have a substituent, a mercapto group, a thioalkoxy group having 2 to 6 carbon atoms that may have a substituent, an amino group, an alkylamino group having 1 to 6 carbon atoms that may have a substituent, a carboxy group, an alkylcarbonyloxy group having 1 to 6 carbon atoms that may have a substituent, a carbamoyloxy group that may have a substituent, or an alkoxycarbonyloxy group having 2 to 6 carbon atoms that may have a substituent;

$R^3$ to $R^6$ each independently represent a substituent;

m and n each independently represent an integer of 1 to 5, q and r each independently represent an integer of 0 to 4; here, $1 \leq m+q \leq 5$, and $1 \leq n+r \leq 5$ are satisfied;

v is an integer of 0 to 4, w is an integer of 0 or more, a maximum number of w is a maximum number of substituents that may be substituted with a ring formed by X—C=C—Y and Z;

in a case where q is an integer of 2 to 4, a plurality of $R^3$'s may be identical to or different from each other, and the plurality of $R^3$'s may be bonded to each other to form a ring;

in a case where r is an integer of 2 to 4, a plurality of $R^4$'s may be identical to or different from each other, and a plurality of $R^4$'s may be bonded to each other to form a ring;

in a case where v is an integer of 2 to 4, a plurality of $R^5$'s may be identical to or different from each other, but the plurality of $R^5$'s are not bonded to each other to form a ring; and in a case where w is an integer of 2 to 5, a plurality of $R^6$'s may be identical to or different from each other, and the plurality of $R^6$'s may be bonded to each other to form a ring.

[2] The compound according to [1], in which in Formula (1), $R^1$ and $R^2$ each independently represent a group having a hydroxyl group, a mercapto group, an amino group, a polymerizable unsaturated bond, an epoxy group, or an oxetanyl group.

[3] The compound according to [1] or [2], in which in Formula (1), $R^1$ and $R^2$ each independently represent a group represented by Formula (2);

in Formula (2), $L^1$ represents —O—, —S—, or —NH—, Alkylene represents an alkylene group having 2 to 6 carbon atoms, $L^2$ represents —O—, —S—, or —NH—, n1 represents an integer of 0 to 2, P is a hydrogen atom or a group represented by any one of Formulae (P1) to (P4); and

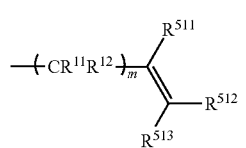

Formula (P1)

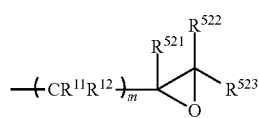

Formula (P2)

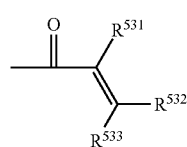

Formula (P3)

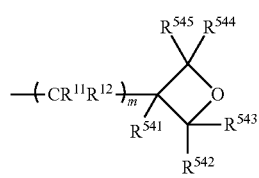

Formula (P4)

in Formulae (P1) to (P4), $R^{511}$, $R^{512}$, $R^{513}$, $R^{521}$, $R^{522}$, $R^{523}$, $R^{531}$, $R^{532}$, $R^{533}$, $R^{541}$, $R^{542}$, $R^{543}$, $R^{544}$, and $R^{545}$ each independently represent a hydrogen atom or an alkyl group, m represents an integer of 0 to 2, and $R^{11}$ and $R^{12}$ each independently represent a hydrogen atom or a substituent.

[4] The compound according to any one of [1] to [3], in which, in Formula (1), at least one selected from X and Y is a nitrogen atom.

[5] The compound according to any one of [1] to [4], in which, in Formula (1), $R^1$ and $R^2$ are the same group.

[6] The compound according to [1], which is represented by Formula (3);

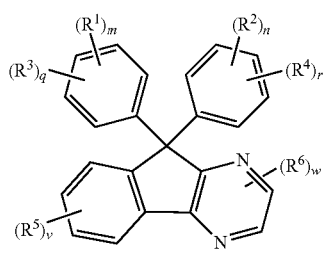

Formula (3)

in Formula (3), $R^1$ and $R^2$ each independently represent a hydroxyl group, an alkoxy group having 2 to 6 carbon atoms that may have a substituent, a mercapto group, a thioalkoxy group having 2 to 6 carbon atoms that may have a substituent, an amino group, an alkylamino group having 1 to 6 carbon atoms that may have a substituent, a carboxy group, an alkylcarbonyloxy group having 1 to 6 carbon atoms that may have a substituent, a carbamoyloxy group that may have a substituent, or an alkoxycarbonyloxy group having 2 to 6 carbon atoms that may have a substituent;

$R^3$ to $R^6$ each independently represent a substituent;

m and n each independently represent an integer of 1 to 5, q and r each independently represent an integer of 0 to 4; here, $1 \leq m+q \leq 5$, and $1 \leq n+r \leq 5$ are satisfied;

v is an integer of 0 to 4, and w is an integer of 0 to 2;

in a case where q is an integer of 2 to 4, a plurality of $R^3$'s may be identical to or different from each other, and the plurality of $R^3$'s may be bonded to each other to form a ring;

in a case where r is an integer of 2 to 4, a plurality of $R^4$'s may be identical to or different from each other, and the plurality of $R^4$'s may be bonded to each other to form a ring;

in a case where v is an integer of 2 to 4, a plurality of $R^5$'s may be identical to or different from each other, but the plurality of $R^5$'s are not bonded to each other to form a ring; and in a case where w is 2, a plurality of $R^6$'s may be identical to or different from each other, and the plurality of $R^6$'s may be bonded to each other to form a ring.

[7] The compound according to any one of [1] to [6], in which $R^1$ and $R^2$ are each independently represented by Formula (4);

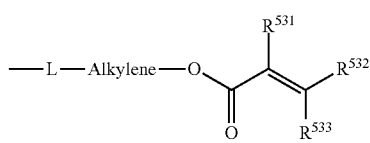

Formula (4)

in Formula (4), L represents —O—, —S—, or —NH—, Alkylene represents an alkylene group having 2 to 6 carbon atoms, and $R^{531}$, $R^{532}$, and $R^{533}$ each independently represent a hydrogen atom or an alkyl group.

[8] A curable composition comprising the compound according to any one of [1] to [7].

[9] The curable composition according to [8], in which the curable composition contains a (meth)acrylate monomer and at least one selected from a photoradical polymerization initiator and a thermal radical polymerization initiator.

[10] The curable composition according to [9], in which viscosity of the (meth)acrylate monomer of the curable composition at 25° C. is less than 2,000 mPa·s.

[11] A cured product of the curable composition according to any one of [8] to [10].

[12] An optical member comprising the cured product according to [11].

[13] A lens comprising the cured product according to [11].

According to the present invention, it is possible to obtain a compound that may form a cured product having a low Abbe number and a high abnormal dispersibility. The cured product formed from a curable composition including the compound of the present invention is preferably used as an optical member.

DESCRIPTION OF THE PREFERRED EMBODIMENTS

Hereinafter, the present invention is specifically described. The following description of components may be made based on a representative embodiment or a specific example, but the present invention is not limited to the embodiment. According to the present specification, the numerical range expressed by using "to" means a range including numerical values described before and after "to" as a lower limit value and an upper limit value.

In the present specification, "(meth)acrylate" represents acrylate and methacrylate, and "(meth)acryloyl" means acryloyl and methacryloyl. The monomer according to the present invention is different from an oligomer and a polymer and refers to a compound having a weight-average molecular weight of 1,000 or less.

In the present specification, with respect to a group (atomic group), in a case where substitution or unsubstitution is not described, the group includes both of a group having a substituent and a group not having a substituent. For example, an "alkyl group" includes not only an alkyl group not having a substituent (unsubstituted alkyl group) but also an alkyl group having a substituent (substituted alkyl group).

(Compound)

The present invention relates to a compound represented by Formula (1).

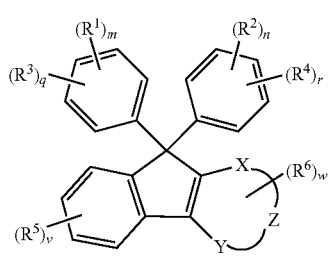

Formula (1)

In Formula (1), X and Y each independently represent an oxygen atom, a sulfur atom, a nitrogen atom, or a carbon atom, and at least one of X or Y is an oxygen atom, a sulfur atom, or a nitrogen atom. Z is an atomic group that forms a 5 to 7-membered ring together with X—C=C—Y and represents an atomic group including at least one selected from a carbon atom and a heteroatom.

$R^1$ and $R^2$ each independently represent a hydroxyl group, an alkoxy group having 2 to 6 carbon atoms that may have a substituent, a mercapto group, a thioalkoxy group having 2 to 6 carbon atoms that may have a substituent, an amino group, an alkylamino group having 1 to 6 carbon atoms that may have a substituent, a carboxy group, an alkylcarbonyloxy group having 1 to 6 carbon atoms that may have a substituent, a carbamoyloxy group that may have a substituent, or an alkoxycarbonyloxy group having 2 to 6 carbon atoms that may have a substituent.

$R^3$ to $R^6$ each independently represent a substituent.

m and n each independently represent an integer of 1 to 5, and q and r each independently represent an integer of 0 to 4. Here, $1 \leq m+q \leq 5$, and $1 \leq n+r \leq 5$ are satisfied.

v is an integer of 0 to 4, w is an integer of 0 or more, and a maximum number of w is a maximum number of substituents that may be substituted with rings formed by X—C=C—Y and Z.

In a case where q is an integer of 2 to 4, a plurality of $R^3$'s may be identical to or different from each other, and the plurality of $R^3$'s may be bonded to each other to form a ring.

In a case where r is an integer of 2 to 4, a plurality of $R^4$'s may be identical to or different from each other, and the plurality of $R^4$'s may be bonded to each other to form a ring.

In a case where v is an integer of 2 to 4, a plurality of $R^5$'s may be identical to or different from each other, but the plurality of $R^5$'s are not bonded to each other to form a ring.

in a case where w is an integer of 2 to 5, a plurality of $R^6$'s may be identical to or different from each other, and the plurality of $R^6$'s may be bonded to each other to form a ring.

In Formula (1), X and Y each independently represent an oxygen atom, a sulfur atom, a nitrogen atom, or a carbon atom, and at least one of X or Y is an oxygen atom, a sulfur atom, or a nitrogen atom. X and Y each independently and preferably represent a nitrogen atom or a carbon atom, and at least one selected from X and Y is preferably a nitrogen atom. It is preferable that both of X and Y are nitrogen atoms.

In Formula (1), Z is an atomic group that forms a 5 to 7-membered ring together with X—C=C—Y and represents an atomic group including at least one selected from a carbon atom and a heteroatom. Z is preferably an atomic group that forms a 5 or 6-membered ring together with X—C=C—Y and is more preferably an atomic group that forms a 6-membered ring. Z may be an atomic group including at least one selected from a carbon atom and a heteroatom, is preferably an atomic group including a carbon atom, and more preferably an atomic group including a carbon atom.

In Formula (1), $R^1$ and $R^2$ each independently represent a hydroxyl group, an alkoxy group having 2 to 6 carbon atoms that may have a substituent, a mercapto group, a thioalkoxy group having 2 to 6 carbon atoms that may have a substituent, an amino group, an alkylamino group having 1 to 6 carbon atoms that may have a substituent, a carboxy group, an alkylcarbonyloxy group having 1 to 6 carbon atoms that may have a substituent, a carbamoyloxy group that may have a substituent, or an alkoxycarbonyloxy group having 2 to 6 carbon atoms that may have a substituent.

The substituents are not particularly limited, and examples thereof include a halogen atom, a halogenated alkyl group, an alkyl group, an alkenyl group, an acyl group, a hydroxyl group, a hydroxyalkyl group, an alkoxy group, an aryl group, a heteroaryl group, an alicyclic group, a cyano group, an epoxy group, an oxetanyl group, a mercapto group, an amino group, and a (meth)acryloyl group. The substituents may further have the substituent, and a carbon atom in a substituent may be substituted with an oxygen atom. In a case where $R^1$ and $R^2$ is an alkoxy group having 2 to 6 carbon atoms, a thioalkoxy group having 2 to 6 carbon atoms, an alkylamino group having 1 to 6 carbon atoms, an alkylcarbonyloxy group having 1 to 6 carbon atoms, a carbamoyloxy group, and an alkoxycarbonyloxy group having 2 to 6 carbon atoms, it is preferable that the polymerizable group has a substituent.

It is preferable that $R^1$ and $R^2$ each independently represent a group having a hydroxyl group, a mercapto group, an amino group, a polymerizable unsaturated bond, an epoxy group, or an oxetanyl group. $R^1$ and $R^2$ may be each independently a hydroxyl group, a mercapto group, an amino group, or a polymerizable unsaturated group.

It is preferable that $R^1$ and $R^2$ each independently represent a group represented by Formula (2).

$$-L^1-(\text{Alkylene-}L^2)_{n1}P \quad \text{Formula (2)}$$

In Formula (2), $L^1$ represents —O—, —S—, or —NH—, Alkylene represents an alkylene group having 2 to 6 carbon atoms, $L^2$ represents —O—, —S—, or —NH—, n1 represents an integer of 0 to 2, and P is a hydrogen atom or a group represented by any one of Formulae (P1) to (P4).

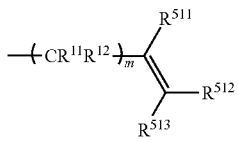

Formula (P1)

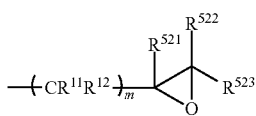

Formula (P2)

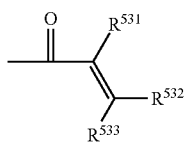

Formula (P3)

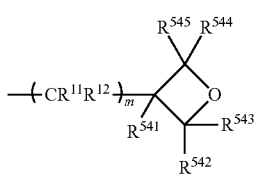

Formula (P4)

In Formulae (P1) to (P4), $R^{511}$, $R^{512}$, $R^{513}$, $R^{521}$, $R^{522}$, $R^{523}$, $R^{531}$, $R^{532}$, $R^{533}$, $R^{541}$, $R^{542}$, $R^{543}$, $R^{544}$, and $R^{545}$ each independently represent a hydrogen atom or an alkyl group, m represents an integer of 0 to 2, and $R^{11}$ and $R^{12}$ each independently represent a hydrogen atom or a substituent.

In Formula (2), $L^1$ represents —O—, —S—, or —NH—, and is preferably —O—. Alkylene represents an alkylene group having 2 to 6 carbon atoms, is preferably an alkylene group having 2 to 4 carbon atoms, and more preferably an alkylene group having 2 carbon atoms.

In Formula (2), $L^2$ represents —O—, —S—, or —NH—, and is preferably —O—. n1 represents an integer of 0 to 2 and is preferably 0 or 1. P is a hydrogen atom or a group represented by any one of Formulae (P1) to (P4), is more preferably a group represented by any one of Formulae (P1) to (P4), and even more preferably a group represented by Formula (P3).

In Formulae (P1) to (P4), $R^{511}$, $R^{512}$, $R^{513}$, $R^{521}$, $R^{522}$, $R^{523}$, $R^{531}$, $R^{532}$, $R^{533}$, $R^{541}$, $R^{542}$, $R^{543}$, $R^{544}$, and $R^{545}$ each independently and preferably represent a hydrogen atom or an alkyl group having 1 to 6 carbon atoms, and more preferably represent a hydrogen atom or an alkyl group having 1 to 3 carbon atoms. Among these, $R^{511}$, $R^{512}$, $R^{513}$, $R^{521}$, $R^{522}$, $R^{523}$, $R^{531}$, $R^{532}$, $R^{533}$, $R^{541}$, $R^{542}$, $R^{543}$, $R^{544}$, and $R^{545}$ each independently and preferably represent hydrogen atoms, and $R^{541}$ is preferably an alkyl group having 1 to 3 carbon atoms.

In Formulae (P1) to (P4), m represents an integer of 0 to 2 and is preferably an integer of 0 or 1. $R^{11}$ and $R^{12}$ each independently represent a hydrogen atom or a substituent, is preferably a hydrogen atom or an alkyl group, and more preferably a hydrogen atom. In a case where $R^{11}$ and $R^{12}$ are substituents, examples of preferable substituents include the substituents as above.

It is preferable that $R^1$ and $R^2$ each independently represent a group represented by Formula (4).

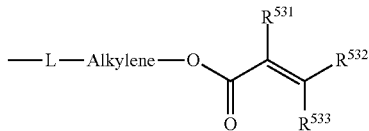

Formula (4)

In Formula (4), L represents —O—, —S—, or —NH—, Alkylene represents an alkylene group having 2 to 6 carbon atoms, and $R^{531}$, $R^{532}$, and $R^{533}$ each independently represent a hydrogen atom or an alkyl group.

In Formula (4), L is preferably —O—. Alkylene represents an alkylene group having 2 to 6 carbon atoms, is preferably an alkylene group having 2 to 4 carbon atoms, and more preferably an alkylene group having 2 carbon atoms. $R^{531}$, $R^{532}$, and $R^{533}$ each are preferably a hydrogen atom or an alkyl group having 1 to 6 carbon atoms, more preferably a hydrogen atom or an alkyl group having 1 to 3 carbon atoms, and even more preferably a hydrogen atom.

In Formula (1), $R^1$ and $R^2$ may be different groups, but it is preferable that $R^1$ and $R^2$ are the same group.

In Formula (1), $R^3$ to $R^6$ each independently represent a substituent. The substituents represented by $R^3$ to $R^6$ are not particularly limited, and examples thereof include a halogen atom, a halogenated alkyl group, an alkyl group, an alkenyl group, an acyl group, a hydroxyl group, a hydroxyalkyl group, an alkoxy group, an aryl group, a heteroaryl group, an alicyclic group, and a cyano group. The substituent represented by $R^3$ to $R^6$ is preferably a halogen atom, an alkyl group, an alkoxy group, an aryl group, or a cyano group, more preferably a halogen atom, an alkyl group having 1 to 5 carbon atoms, an alkoxy group having 1 to 5 carbon atoms, a phenyl group, or a cyano group, and particularly preferably a halogen atom, a methyl group, a methoxy group, a phenyl group, or a cyano group.

Among these, it is preferable that $R^3$ and $R^4$ each independently represent a methyl group or a methoxy group. A plurality of $R^3$'s or a plurality of $R^4$'s may form rings, respectively, and in this case, may form a fused ring with a substituted ring. $R^5$ is preferably a halogen atom, a methyl group or a methoxy group. $R^6$ is preferably a halogen atom, a methyl group, a methoxy group, or a cyano group. The plurality of $R^6$'s are more preferably a group forming a fused ring with a substituted ring.

It is preferable that the substituent represented by $R^3$ to $R^6$ is not a polymerizable group.

In Formula (1), m and n each independently represent an integer of 1 to 5, and q and r each independently represent an integer of 0 to 4. Here, $1 \le m+q \le 5$, and $1 \le n+r \le 5$ are satisfied.

m and n each independently and preferably represent an integer of 1 to 3, more preferably represent 1 or 2, and even more preferably represent 1. q and r each independently and preferably represent an integer of 0 to 3, more preferably an integer of 0 to 2, and even more preferably 0.

v is an integer of 0 to 4, w is an integer of 0 or more, and a maximum number of w is a maximum number of substituents that may be substituted with rings formed by X—C=C—Y and Z.

v is preferably an integer of 0 to 3, more preferably an integer of 0 to 2, and even more preferably 0. w is preferably an integer of 0 to 3 and more preferably an integer of 0 to 2.

In a case where q is an integer of 2 to 4, a plurality of $R^3$'s may be identical to or different from each other. The plurality of $R^3$ may be bonded to each other to form a ring, but it is preferable that the plurality of $R^3$'s are not bonded to each other to form a ring. In a case where r is an integer of 2 to 4, a plurality of $R^4$'s may be identical to or different from each other. The plurality of $R^4$'s may be bonded to each other to form a ring, but it is preferable that the plurality of $R^4$'s are not bonded to each other to form a ring.

In a case where v is an integer of 2 to 4, a plurality of $R^5$'s may be identical to or different from each other, but the plurality of $R^5$'s are not bonded to each other to form a ring.

In a case where w is an integer of 2 to 5, a plurality of $R^6$'s may be identical to or different from each other, and the plurality of $R^6$'s may be bonded to each other to form a ring. In a case where w is an integer of 2 to 5, the plurality of $R^6$'s are bonded to each other and are preferably a group that forms a fused ring together with a substituted ring. The fused ring may further have a substituent, and in this case, as the substituent, the substituents exemplified as $R^6$ may be exemplified as preferable substituents.

In a case where the plurality of $R^6$'s are bonded to each other and are groups for forming a fused ring together with a substituted ring, the number of rings for forming a fused ring is preferably 4 or less, more preferably 3 or less, and even more preferably 2. In a case where the number of rings for forming a fused ring is in the above range, the coloration of the cured product including the compound is easily suppressed.

The compound is preferably a compound represented by Formula (3).

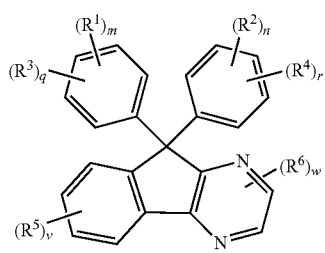

Formula (3)

In Formula (3), $R^1$ and $R^2$ each independently represent a hydroxyl group, an alkoxy group having 2 to 6 carbon atoms that may have a substituent, a mercapto group, a thioalkoxy group having 2 to 6 carbon atoms that may have a substituent, an amino group, an alkylamino group having 1 to 6 carbon atoms that may have a substituent, a carboxy group, an alkylcarbonyloxy group having 1 to 6 carbon atoms that may have a substituent, a carbamoyloxy group that may have a substituent, or an alkoxycarbonyloxy group having 2 to 6 carbon atoms that may have a substituent.

$R^3$ to $R^6$ each independently represent a substituent.

m and n each independently represent an integer of 1 to 5, and q and r each independently represent an integer of 0 to 4. Here, $1 \leq m+q \leq 5$, and $1 \leq n+r \leq 5$ are satisfied.

v is an integer of 0 to 4, and w is an integer of 0 to 2.

In a case where q is an integer of 2 to 4, a plurality of $R^3$'s may be identical to or different from each other, and the plurality of $R^3$'s may be bonded to each other to form a ring.

In a case where r is an integer of 2 to 4, a plurality of $R^4$'s may be identical to or different from each other, and a plurality of $R^4$'s may be bonded to each other to form a ring.

In a case where v is an integer of 2 to 4, a plurality of $R^5$'s may be identical to or different from each other, but the plurality of $R^5$'s are not bonded to each other to form a ring.

In a case where w is 2, a plurality of $R^6$'s may be identical to or different from each other, and the plurality of $R^6$'s may be bonded to each other to form a ring.

The preferable ranges of $R^1$ and $R^2$ in Formula (3) are respectively the same as those of $R^1$ and $R^2$ in Formula (1).

The preferable ranges of $R^3$ to $R^6$ in Formula (3) are respectively the same as those of $R^3$ to $R^6$ in Formula (1).

The preferable ranges of m, n, q, r, v, and w in Formula (3) are respectively the same as those of m, n, q, r, v, and w in Formula (1).

Hereinafter, specific examples of the compound represented by Formula (1) preferably used in the present invention are provided, but the present invention is not limited to the following compounds. In the following specific examples, the structure of the compound represented by Formula (1) is divided into partial structures of A to C, and each partial structure is listed as shown in the following structural formula. That is, specific examples of the compound represented by Formula (1) include a structure obtained by combining the structures exemplified as the partial structures A to C.

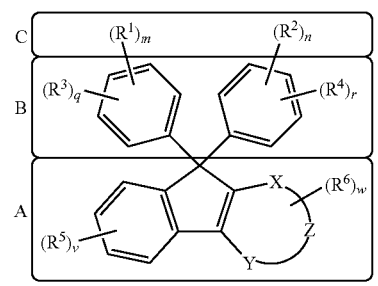

Specific Examples of Partial Structure of A

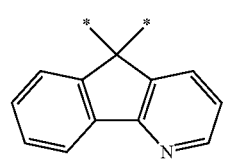

(A-1)

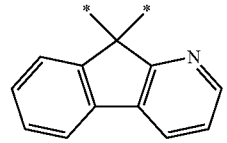

(A-2)

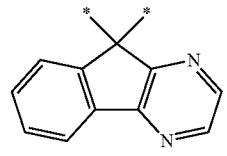

(A-3)

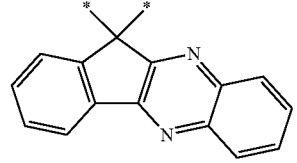

(A-4)

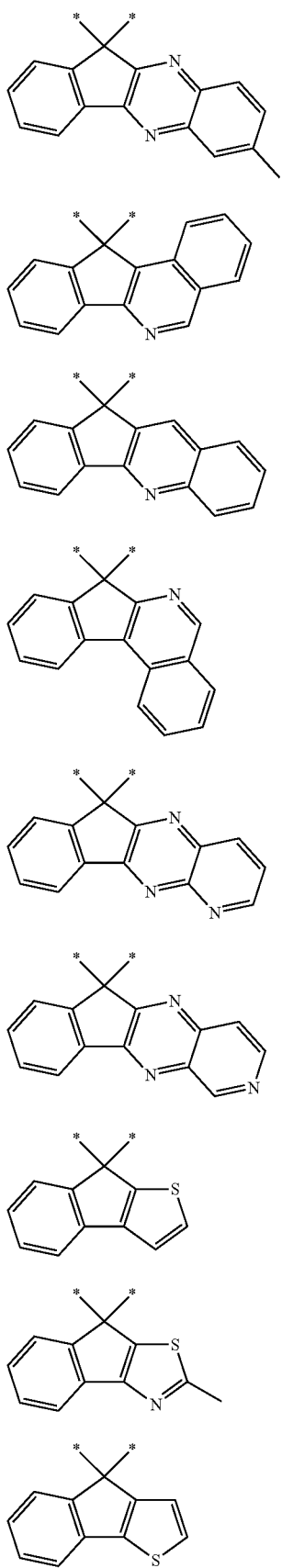
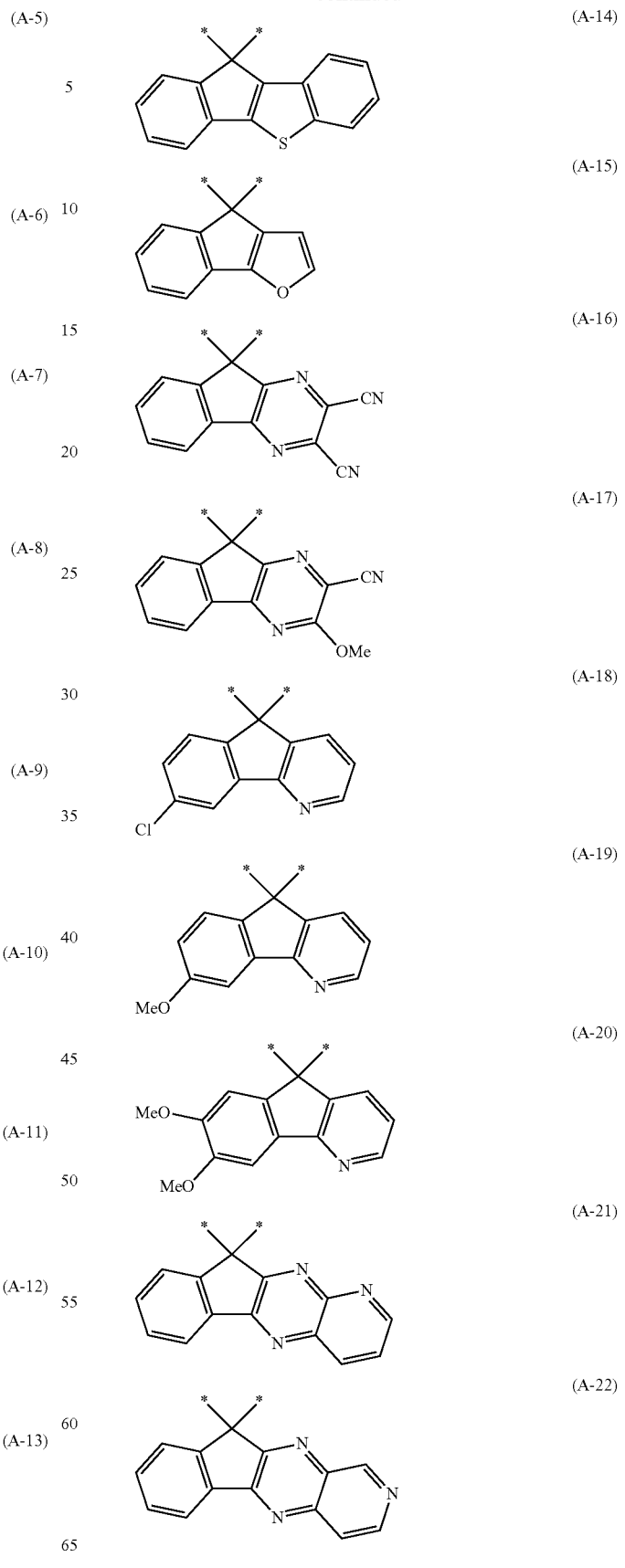

Specific Examples of Partial Structure of A

In the structural formulae of the specific examples of the partial structure of A, * represents a linking portion to the partial structure B. MeO represents a methoxy group.

Specific Examples of Partial Structure of B

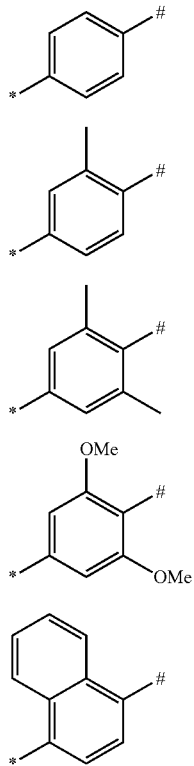

(B-1)
(B-2)
(B-3)
(B-4)
(B-5)

Specific Examples of Partial Structure of B

In the structural formulae of the specific examples of the partial structure of B, * represents a linking portion to the partial structure A, and # represents a linking portion to the partial structure C. The specific examples are specific examples of one ring structural unit out of two ring structural units included in the partial structure B, and two ring structural units included in the partial structure B may be the same structural units or may be structural units different from each other. MeO represents a methoxy group.

Specific Examples of Partial Structure of C

—OH (C-1)

—SH (C-2)

—NH₂ (C-3)

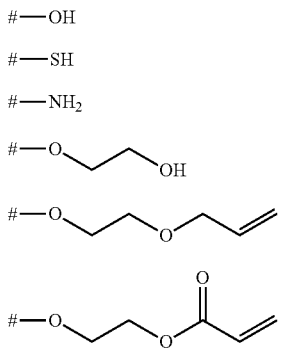

(C-4)
(C-5)
(C-6)

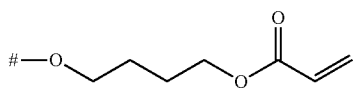
(C-7)

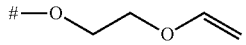
(C-8)

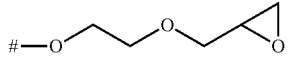
(C-9)

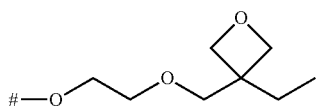
(C-10)

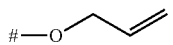
(C-11)

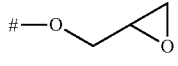
(C-12)

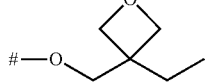
(C-13)

In the structural formulae of the specific examples of the partial structure of C, # represents a linking portion to the partial structure B. The specific examples are specific examples of one ring structural unit out of two ring structural units included in the partial structure C, and two ring structural units included in the partial structure C may be the same structural units or may be structural units different from each other.

Among these, the compound represented by Formula (1) is preferably any one of Compounds (1) to (61).

TABLE 1

| | Partial structure A | Partial structure B | Partial structure C |
|---|---|---|---|
| Compound (1) | A-1 | B-1 | C-1 |
| Compound (2) | A-2 | B-1 | C-1 |
| Compound (3) | A-3 | B-1 | C-1 |
| Compound (4) | A-4 | B-1 | C-1 |
| Compound (5) | A-5 | B-1 | C-1 |
| Compound (6) | A-6 | B-1 | C-1 |
| Compound (7) | A-7 | B-1 | C-1 |
| Compound (8) | A-8 | B-1 | C-1 |
| Compound (9) | A-9 | B-1 | C-1 |
| Compound (10) | A-10 | B-1 | C-1 |
| Compound (11) | A-11 | B-1 | C-1 |
| Compound (12) | A-12 | B-1 | C-1 |
| Compound (13) | A-13 | B-1 | C-1 |
| Compound (14) | A-14 | B-1 | C-1 |
| Compound (15) | A-15 | B-1 | C-1 |
| Compound (16) | A-16 | B-1 | C-1 |
| Compound (17) | A-17 | B-1 | C-1 |
| Compound (18) | A-18 | B-1 | C-1 |
| Compound (19) | A-19 | B-1 | C-1 |
| Compound (20) | A-20 | B-1 | C-1 |
| Compound (21) | A-1 | B-1 | C-6 |
| Compound (22) | A-2 | B-1 | C-6 |
| Compound (23) | A-3 | B-1 | C-6 |
| Compound (24) | A-4 | B-1 | C-6 |
| Compound (25) | A-5 | B-1 | C-6 |
| Compound (26) | A-6 | B-1 | C-6 |
| Compound (27) | A-7 | B-1 | C-6 |
| Compound (28) | A-8 | B-1 | C-6 |
| Compound (29) | A-9 | B-1 | C-6 |

TABLE 1-continued

|  | Partial structure A | Partial structure B | Partial structure C |
|---|---|---|---|
| Compound (30) | A-10 | B-1 | C-6 |
| Compound (31) | A-11 | B-1 | C-6 |
| Compound (32) | A-12 | B-1 | C-6 |
| Compound (33) | A-13 | B-1 | C-6 |
| Compound (34) | A-14 | B-1 | C-6 |
| Compound (35) | A-15 | B-1 | C-6 |
| Compound (36) | A-16 | B-1 | C-6 |
| Compound (37) | A-17 | B-1 | C-6 |
| Compound (38) | A-18 | B-1 | C-6 |
| Compound (39) | A-19 | B-1 | C-6 |
| Compound (40) | A-20 | B-1 | C-6 |
| Compound (41) | A-4 | B-1 | C-2 |
| Compound (42) | A-4 | B-1 | C-3 |
| Compound (43) | A-4 | B-1 | C-4 |
| Compound (44) | A-4 | B-1 | C-5 |
| Compound (45) | A-4 | B-1 | C-7 |
| Compound (46) | A-4 | B-1 | C-8 |
| Compound (47) | A-4 | B-1 | C-9 |
| Compound (48) | A-4 | B-1 | C-10 |
| Compound (49) | A-4 | B-3 | C-1 |
| Compound (50) | A-4 | B-2 | C-6 |
| Compound (51) | A-4 | B-3 | C-6 |
| Compound (52) | A-4 | B-4 | C-6 |
| Compound (53) | A-4 | B-5 | C-6 |
| Compound (54) | A-16 | B-1 | C-3 |
| Compound (55) | A-21 | B-1 | C-1 |
| Compound (56) | A-22 | B-1 | C-1 |
| Compound (57) | A-21 | B-1 | C-6 |
| Compound (58) | A-22 | B-1 | C-6 |
| Compound (59) | A-4 | B-1 | C-11 |
| Compound (60) | A-4 | B-1 | C-12 |
| Compound (61) | A-4 | B-1 | C-13 |

Among the structures, the partial structure A is preferably (A-4), (A-7), (A-9), (A-10), (A-16), (A-21), or (A-22), more preferably (A-4), (A-9), or (A-10), and particularly preferably (A-4). The partial structure B is preferably (B-1) or (B-3) and more preferably (B-1). The partial structure C is preferably (C-1), (C-3), (C-6), or (C-7), more preferably (C-1), (C-6), or (C-7), and particularly preferably (C-6).

The molecular weight of the compound represented by Formula (1) is preferably 400 to 1,000, more preferably 500 to 900, and particularly preferably 550 to 800.

As clearly understood from the specific examples of Formula (1) and the partial structure A, the compound of the present invention is an asymmetric structure. In a case where the compound of the present invention has this structure, the crystallization of the compound is suppressed, and solubility with respect to the (meth)acrylate monomer described below may be improved.

The method of obtaining the compound represented by Formula (1) may be particularly limited, and the compound may be commercially obtained and may be manufactured by synthesis. In a case where the compound is manufactured by synthesis, the method of manufacturing the compound represented by Formula (1) is not particularly limited, and the compound may be synthesized by well-known methods and methods described in examples.

(Curable Composition)

The present invention relates to a curable composition containing the compound. Since the curable composition of the present invention contains a compound having a specific structure, it is possible to form a cured product having a low Abbe number. The curable composition of the present invention may form a cured product having a high abnormal dispersibility.

The Abbe number (νD) and the abnormal dispersibility (θg, F) of the cured product formed from the curable composition are values measured by using an Abbe refractometer (manufactured by Kalnew Optical Industrial Co., Ltd.). Specifically, the curable composition is introduced into a transparent glass mold having a diameter of 10 mm and a thickness of 1 mm and was heated to 200° C. in an atmosphere having an oxygen concentration of 1% or less or irradiated with ultraviolet rays, so as to manufacture a cured product, and the Abbe number (νD) and the abnormal dispersibility (θg, F) of this cured product are measured. The Abbe number (νD) and the abnormal dispersibility (θg, F) of the cured product are calculated from the following equation.

$$\nu D = (nD-1)/(nF-nC)$$

$$\theta g, F = (ng-nF)/(nF-nC)$$

Here, nD is a refractive index at a wavelength of 589 nm, nF is a refractive index at a wavelength of 486 nm, nC is a refractive index at a wavelength of 656 nm, and ng is a refractive index at a wavelength of 435.8 nm.

In a case where the Abbe number of the cured product is suppressed to be low, it is possible to correct the chromatic aberration in the entire wavelength range. In order to increase the abnormal dispersibility of the cured product, it is possible to effectively correct the chromatic aberration particularly at a shorter wavelength.

The content of the compound represented by Formula (1) in the curable composition is preferably 20 to 94 mass %, more preferably 40 to 85 mass %, and even more preferably 50 to 85 mass % with respect to the total mass of the curable composition. In a case where the content of the compound is caused to be in the range, the low Abbe number and the high abnormal dispersibility of the cured product may be easily achieved. In a case where the lower limit value of the content of the compound in a case of including an acrylate structure in the partial structure C of the compound is 50 mass %, the surface transferability during forming of a cured product may be increased. In a case where the surface transferability is satisfactory, generation of fine irregularities (wrinkles) on the surface of the cured product is suppressed, and a cured product having high quality may be formed.

In the curable composition, two or more kinds of compounds represented by Formula (1) may be contained. In a case where two or more kinds of compounds represented by Formula (1) are contained, it is preferable that the total content is in the above range.

The viscosity of the curable composition preferably 20,000 mPa·s or less, more preferably 15,000 mPa·s or less, even more preferably 13,000 mPa·s or less, and particularly preferably 10,000 mPa·s or less. In a case where the viscosity of the curable composition becomes in the range, handleability during forming of a cured product may be increased and a cured product having a high quality may be formed.

The curable composition of the present invention preferably includes the following components in addition to the above compound. For example, the curable composition preferably contains a (meth)acrylate monomer and at least one kind selected from a photoradical polymerization initiator and a thermal radical polymerization initiator.

((Meth)Acrylate Monomer)

The curable composition of the present invention preferably includes a (meth)acrylate monomer. The (meth)acrylate monomer may be a monofunctional (meth)acrylate monomer having one (meth)acryloyl group in a molecule and may be a polyfunctional (meth)acrylate monomer having two or more (meth)acryloyl groups in a molecule. Among these, a monofunctional (meth)acrylate monomer is preferably used.

The viscosity of the (meth)acrylate monomer at 25° C. is preferably less than 2,000 mPa·s. The viscosity of the (meth)acrylate monomer at 25° C. is more preferably less than 1,500 mPa·s, even more preferably less than 1,000 mPa·s, still even more preferably less than 500 mPa·s, and particularly preferably less than 200 mPa·s. The viscosity of the (meth)acrylate monomer at 25° C. is a value measured in the conditions of 25° C. and a shear rate of $10 \text{ s}^{-1}$ by using a rheometer (RS600) manufactured by HAAKE Inc.

Examples of the monofunctional (meth)acrylate monomer used in the present invention include adamantyl (meth)acrylates such as 1-adamantyl (meth)acrylate, norbornyl (meth)acrylates such as isobornyl (meth)acrylate, tricyclodecane (meth)acrylates such as tricyclo $[5,2,1,0^{2,6}]$ deca-8-yl acrylate, 2-ethyl-2-butylpropanediol (meth)acrylate, 2-ethylhexyl (meth)acrylate, 2-ethylhexyl carbitol (meth)acrylate, 2-hydroxybutyl (meth)acrylate, 2-hydroxyethyl (meth)acrylate, 2-hydroxypropyl (meth)acrylate, 2-methoxyethyl (meth)acrylate, 3-methoxybutyl (meth)acrylate, 4-hydroxybutyl (meth)acrylate, benzyl (meth)acrylate, butanediol mono(meth)acrylate, butoxyethyl (meth)acrylate, butyl (meth)acrylate, cetyl (meth)acrylate, ethylene oxide (EO)-modified cresol (meth)acrylate, dipropylene glycol (meth)acrylate, ethoxylated phenyl (meth)acrylate, ethyl (meth)acrylate, isoamyl (meth)acrylate, isobutyl (meth)acrylate, isooctyl (meth)acrylate, cyclohexyl (meth)acrylate, dicyclopentanyl (meth)acrylate, dicyclopentanyloxyethyl (meth)acrylate, isomyristyl (meth)acrylate, lauryl (meth)acrylate, methoxydipropylene glycol (meth)acrylate, methoxytripropylene glycol (meth)acrylate, methoxy polyethylene glycol (meth)acrylate, methoxytriethylene glycol (meth)acrylate, methyl (meth)acrylate, neopentyl glycol benzoate (meth)acrylate, nonylphenoxy polyethylene glycol (meth)acrylate, nonylphenoxy polypropylene glycol (meth)acrylate, octyl (meth)acrylate, para cumyl phenoxy ethylene glycol (meth)acrylate, epichlorohydrin (ECH)-modified phenoxy (meth)acrylate, phenoxyethyl (meth)acrylate, phenoxydiethylene glycol (meth)acrylate, phenoxy hexaethylene glycol (meth)acrylate, phenoxytetraethylene glycol (meth)acrylate, stearyl (meth)acrylate, EO-modified succinic acid (meth)acrylate, tert-butyl (meth)acrylate, tribromophenyl (meth)acrylate, EO-modified tribromophenyl (meth)acrylate, and tridodecyl (meth)acrylate.

The (meth)acrylate monomer is preferably a (meth)acrylate monomer including an aryl group or a heteroaryl group. Among these, the (meth)acrylate monomer is more preferably a monofunctional (meth)acrylate monomer including an aryl group or a heteroaryl group. In a case where a (meth)acrylate monomer including an aryl group or a heteroaryl group is used as a (meth)acrylate monomer, the Abbe number of the cured product may be effectively decreased. In a case where a (meth)acrylate monomer including an aryl group or a heteroaryl group is used, it becomes easy to uniformly mixing the (meth)acrylate monomer in the curable composition, and thus it is possible to effectively increase the transparency and the durability of the cured product.

Examples of the (meth)acrylate monomer including an aryl group or a heteroaryl group include benzyl (meth)acrylate, EO-modified cresol (meth)acrylate, ethoxylated phenyl (meth)acrylate, nonylphenoxy polyethylene glycol (meth)acrylate, nonylphenoxy polypropylene glycol (meth)acrylate, para cumyl phenoxy ethylene glycol (meth)acrylate, ECH-modified phenoxy (meth)acrylate, phenoxyethyl (meth)acrylate, phenoxydiethylene glycol (meth)acrylate, phenoxy hexaethylene glycol (meth)acrylate, phenoxytetraethylene glycol (meth)acrylate, tribromophenyl (meth)acrylate, EO-modified tribromophenyl (meth)acrylate, O-phenyl phenol (meth)acrylate, and O-phenyl phenol EO-modified (meth)acrylate. Among these, benzyl (meth)acrylate, phenoxyethyl (meth)acrylate, O-phenyl phenol (meth)acrylate, and O-phenyl phenol EO-modified (meth)acrylate are more preferable, benzyl (meth)acrylate and phenoxyethyl (meth)acrylate are particularly preferable, and benzyl acrylate and phenoxyethyl acrylate are more particularly preferable.

The (meth)acrylate monomer may be an alicyclic (meth)acrylate monomer. The alicyclic (meth)acrylate monomer may be a monomer obtained by bonding one (meth)acryloyl group to an aliphatic ring directly or via a divalent linking group or may be a monomer obtained by bonding two or more (meth)acryloyl groups to an aliphatic ring directly or via a divalent linking group. Among these, a monofunctional (meth)acrylate monomer to which one (meth)acryloyl group is directly bonded to an aliphatic ring is preferably used.

The aliphatic ring may have a single ring structure, may have a polycyclic structure in which two or more aliphatic rings are linked or fused, or may have bridged ring hydrocarbon. The aliphatic ring may only include a carbon atom and a hydrogen atom or may have a heteroatom in addition to a carbon atom and a hydrogen atom. The number of carbon atoms of the aliphatic ring is not particularly limited, but is preferably 6 to 20, more preferably 7 to 15, and even more preferably 7 to 10. Specifically, the aliphatic ring is preferably tricyclodecane, adamantane, norbornane, cyclohexane, and norbornene, more preferably tricyclodecane, adamantane, and norbornene, and even more preferably tricyclodecane.

Examples of the (meth)acrylate monomer that may be preferably used in the present invention include the following compounds.

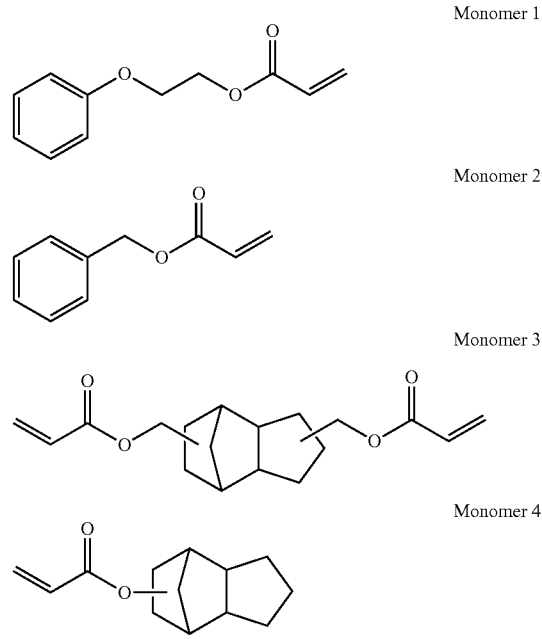

The method of obtaining the (meth)acrylate monomer is not particularly limited, and may be commercially obtained or may be manufactured by synthesis. In a case of being commercially obtained, for example, VISCOAT #192 PEA (Monomer 1) (manufactured by Osaka Organic Chemical Industry Ltd.), VISCOAT #160 BZA (Monomer 2) (manufactured by Osaka Organic Chemical Industry Ltd.), A-DCP (Monomer 3) (manufactured by Shin-Nakamura Chemical Co., Ltd.), and FA-513 AS (Monomer 4) (manufactured by Hitachi Chemical Co., Ltd.) may be preferably used. The viscosity of Monomer 1 at 25° C. and a shear rate of 10 $s^{-1}$ is 9 mPa·s, the viscosity of Monomer 2 at 25° C. and a shear rate of 10 $s^{-1}$ is 8 mPa·s, the viscosity of Monomer 3 at 25° C. and a shear rate of 10 $s^{-1}$ is 120 mPa·s, and the viscosity of Monomer 4 at 25° C. and a shear rate of 10 $s^{-1}$ is 12 mPa·s.

The content of the (meth)acrylate monomer is preferably 5 to 80 mass %, more preferably 5 to 50 mass %, and even more preferably 5 to 40 mass % with respect to the total mass of the curable composition.

(Nonconjugated Vinylidene Group-Containing Compound)

The curable composition of the present invention preferably includes a nonconjugated vinylidene group-containing compound represented by Formula (13) and more preferably includes a nonconjugated vinylidene group-containing compound represented by Formula (14).

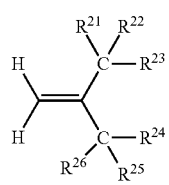

Formula (13)

In Formula (13), $R^{21}$ to $R^{26}$ each independently represent a substituent, at least one of $R^{21}$ to $R^{26}$ forms a ring or at least two thereof may be bonded to each other to form a ring. Here, nonconjugated vinylidene group-containing compound represented by Formula (13) may not include a (meth)acryloyl group.

In Formula (13), the substituent represented by $R^{21}$ to $R^{26}$ are not particularly limited, and examples thereof include a hydrogen atom, a halogen atom, a halogenated alkyl group, an alkyl group, an alkenyl group, an acyl group, a hydroxyl group, a hydroxyalkyl group, an aromatic ring group, a heteroaromatic ring group, and an alicyclic group. Among these, $R^{21}$ to $R^{26}$ each are preferably a hydrogen atom, an alkyl group, and an alkenyl group and more preferably a hydrogen atom, an alkyl group having 1 to 5 carbon atoms, and an alkenyl group having 2 to 5 carbon atoms.

The ring formed by $R^{21}$ to $R^{26}$ may be an aromatic ring, a heteroaromatic ring, or a nonaromatic ring. Among these, the ring formed by $R^{21}$ to $R^{26}$ is preferably a nonaromatic ring and more preferably a nonaromatic hydrocarbon ring. The ring formed by $R^{21}$ to $R^{26}$ may further have a substituent, and as the substituent, an alkyl group having 1 to 5 carbon atoms is preferable, and a methyl group, an ethyl group, an n-propyl group, and an isopropyl group are more preferable. In a case where the ring formed by $R^{21}$ to $R^{26}$ further has a substituent, the substituents may be bonded to each other to form a fused ring.

In the nonconjugated vinylidene group-containing compound represented by Formula (13), $R^{21}$ to $R^{26}$ may form one or a plurality of rings. In a case where $R^{21}$ to $R^{26}$ form a plurality of rings, the rings may be the plurality of rings independent from each other, may be a fused ring obtained by fusing a plurality of rings independent from each other, and may be a fused ring obtained by bonding the substituents in a case where the one ring further has a substituent. Among these, the ring formed by $R^{21}$ to $R^{26}$ is more preferably a fused ring obtained by fusing a plurality of rings and particularly preferably a fused ring obtained by bonding the substituents to each other in a case where one ring further has a substituent. An aspect in which two rings form a spiro-fused is included in a fused ring. Among carbon atoms obtained by bonding $R^{21}$ and $R^{22}$ and carbon atoms obtained by bonding $R^{25}$ and $R^{26}$, one carbon atom is preferably an asymmetric carbon atom.

The nonconjugated vinylidene group-containing compound represented by Formula (13) preferably includes a fused ring obtained by fusing 2 to 5 rings and more preferably includes a fused ring obtained by fusing 2 or 3 rings. The number of ring members of each ring forming the fused ring is preferably 3 to 10, more preferably 3 to 9, particularly preferably 4 to 9.

(A) At least one of $R^{21}$ to $R^{26}$ may form a ring, or (B) at least two thereof may be bonded to each other to form a ring. Among these, the nonconjugated vinylidene group-containing compound is preferably a case where (B) at least two of $R^{21}$ to $R^{26}$ are bonded to each other to form a ring. In this case, the nonconjugated vinylidene group-containing compound is preferably represented by Formula (14).

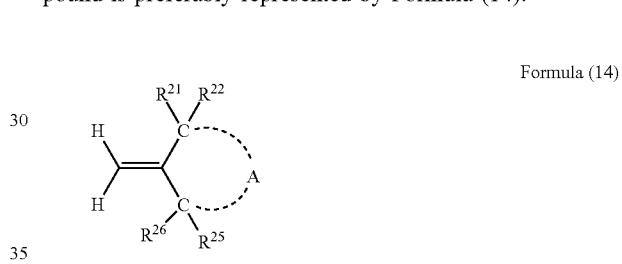

Formula (14)

In Formula (14), $R^{21}$, $R^{22}$, $R^{25}$, and $R^{26}$ each independently represent a substituent, and A represents an atomic group necessary for forming a ring-shaped structure.

In Formula (14), the preferable range of the substituent represented by $R^{21}$, $R^{22}$, $R^{25}$, and $R^{26}$ is the same as that of $R^{21}$ to $R^{26}$ in Formula (13). $R^{21}$, $R^{22}$, $R^{25}$, and $R^{26}$ may be further bonded to each other to form a ring, and this ring may further have a substituent.

Among a set of $R^{21}$ and $R^{22}$ and a set of $R^{25}$ and $R^{26}$, it is preferable that at least one of the two substituents in any one set is a hydrogen atom, and it is more preferable that both of the two substituents in any one set are hydrogen atoms.

$R^{21}$ and $R^{22}$ each independently represent a hydrogen atom or a hydrocarbon group having 1 to 5 carbon atoms, and it is preferable that the hydrocarbon group having 1 to 5 carbon atoms does not form a ring. Only one of $R^{21}$ and $R^{22}$ represents a hydrogen atom or a hydrocarbon group having 1 to 5 carbon atoms, and it is preferable that the hydrocarbon group having 1 to 5 carbon atoms does not form a ring.

In Formula (14), A represents an atomic group necessary for forming a ring-shaped structure, and the ring-shaped structure is not particularly limited and may be a well-known ring-shaped structure. Examples of the ring-shaped structure include an alicyclic (nonaromatic hydrocarbon ring), an aromatic ring, a hetero ring, and a lactone ring including —CO—. Among these, A is preferably an atomic group that includes a carbon atom linked to A of Formula (14) and a carbon atom for forming a nonconjugated vinylidene group and that is necessary for forming an alicyclic ring having 4 to 10 carbon atoms and is particularly preferably an atomic group that includes a carbon atom linked to A of Formula (14) and a carbon atom for forming a nonconjugated vinylidene group and that is necessary for forming an alicyclic ring having 5 to 9 carbon atoms. This alicyclic ring may further have a substituent, and the preferable substituent thereof is the same as the range of the further included substituent that may be included in a ring formed by $R^{21}$, $R^{22}$, $R^{25}$, and $R^{26}$. A may be an unsaturated alicyclic ring or may be a saturated alicyclic ring, but it is preferable that the entire nonconjugated vinylidene group-containing compound represented by Formula (14) generally has at least one unsaturated bond. A may have a substituent represented by $R^{21}$, $R^{22}$, $R^{25}$, and $R^{26}$ and further form a fused ring.

In the present invention, in Formula (14), $R^{21}$, $R^{22}$, $R^{25}$, and $R^{26}$ each independently represent a hydrogen atom or a substituent only including a carbon atom, and A is particularly preferably an alicyclic (nonaromatic hydrocarbon) structure.

According to the present invention, the nonconjugated vinylidene group-containing compound represented by Formula (13) or (14) preferably has another alkenyl group in addition to a vinylidene group (nonconjugated vinylidene group). A position of the vinylidene group in addition to the nonconjugated vinylidene group having the nonconjugated vinylidene group-containing compound represented by Formula (13) or (14) is not particularly limited. Among these, in the nonconjugated vinylidene group-containing compound represented by Formula (13) or (14), a vinylidene group in addition to the nonconjugated vinylidene group is preferably positioned in a ring formed by $R^{21}$, $R^{22}$, $R^{25}$, and $R^{26}$. That is, the ring formed by $R^{21}$, $R^{22}$, $R^{25}$, and $R^{26}$ particularly preferably includes at least one unsaturated hydrocarbon ring and particularly preferably includes an unsaturated hydrocarbon ring having only one double bond.

The molecular weight of the nonconjugated vinylidene group-containing compound is preferably 100 to 400, more preferably 120 to 350, and particularly preferably 130 to 300.

The method of obtaining the nonconjugated vinylidene group-containing compound is not particularly limited, and may be commercially obtained or may be manufactured by synthesis. In a case of being commercially obtained, for example, β-caryophyllene (manufactured by Inoue Perfumery Mfg. Co., Ltd.) and the like may be preferably used.

In a case of being manufactured by synthesis, the method of manufacturing the nonconjugated vinylidene group-containing compound represented by Formula (13) or (14) is not particularly limited and may be synthesized by a well-known method. For example, in a case where β-caryophyllene that may be preferably used in the present invention is synthesized, the synthesis may be performed by methods disclosed in J. Am. Chem. Soc. 85, 362 (1963) and Tetrahedron Letter., 24, 1885 (1983).

The content of the nonconjugated vinylidene group-containing compound is preferably 0.5 to 30 mass %, more preferably 1 to 25 mass %, and even more preferably 2 to 20 mass % with respect to the total mass of the curable composition.

<Photoradical Polymerization Initiator>

The curable composition of the present invention preferably includes at least one selected from a photoradical polymerization initiator and a thermal radical polymerization initiator. The photoradical polymerization initiator is not particularly limited, and well-known photoradical polymerization initiators may be used.

As the photoradical polymerization initiator, specifically, the following compounds may be used. Examples thereof include bis(2,6-dimethoxybenzoyl)-2,4,4-trimethylpentyl-phosphine oxide, bis(2,6-dimethylbenzoyl)-2,4,4-trimethyl-pentylphosphine oxide, bis(2,4,6-trimethylbenzoyl)-2,4,4-trimethylpentylphosphine oxide, bis(2,6-dichlorobenzoyl)-2,4,4-trimethylpentylphosphine oxide, 1-phenyl-2-hydroxy-2 methyl propane-1-one, 1-hydroxycyclohexyl phenyl ketone, 1-(4-isopropylphenyl)-2 hydroxy-2-methyl-propane-1-one, 1,2-diphenylethanedione, methyl phenyl glyoxylate, 1-[4-(2-hydroxyethoxy)-phenyl]-2-hydroxy-2-methyl-1-propane-1-one, 2-hydroxy-1-{4-[4-(2-hydroxy-2-methyl-propionyl)-benzyl]phenyl}-2-methyl-propane-1-one, 2,2-dimethoxy-1,2-diphenylethane-1-one, 2-methyl-1-(4-methylthiophenyl)-2-morpholinopropane-1-one, 2-benzyl-2-dimethylamino-1-(4-morpholinophenyl)-butanone-1,2,4,6-trimethylbenzoyl-diphenyl-phosphine oxide, and bis(2,4,6-trimethylbenzoyl)-phenylphosphine oxide.

Among these, according to the present invention, as the photoradical polymerization initiator, IRGACURE 184 (1-hydroxycyclohexyl phenyl ketone) and IRGACURE 819 (bis(2,4,6-trimethylbenzoyl)-phenylphosphine oxide), manufactured by BASF SE, 1-[4-(2-hydroxyethoxy)-phenyl]-2-hydroxy-2-methyl-1-propane-1-one, 2-methyl-1-(4-methylthiophenyl)-2-morpholinopropane-1-one, and 2,2-dimethoxy-1,2-diphenylethane-1-one may be preferably used.

The content of the photoradical polymerization initiator is preferably 0.01 to 5.0 mass %, more preferably 0.05 to 1.0 mass %, and even more preferably 0.05 to 0.5 mass % with respect to the total mass of the curable composition.

<Thermal Radical Polymerization Initiator>

The curable composition of the present invention preferably includes a thermal radical polymerization initiator. In a case where the thermal radical polymerization initiator is added to the curable composition, in advance, the curable composition is thermally polymerized, so as to form a cured product having high heat resistance.

As the thermal radical polymerization initiator, the following compounds may specifically be used. Examples thereof include 1,1-di(t-hexylperoxy) cyclohexane, 1,1-di(t-butylperoxy) cyclohexane, 2,2-di(4,4-di-(t-butylperoxy) cyclohexyl) propane, t-hexylperoxy isopropyl monocarbonate, t-butylperoxy-3,5,5-trimethylhexanoate, t-butyl peroxylaurate, dicumyl peroxide, di-t-butyl peroxide, t-butylperoxy-2-ethylhexanoate, t-hexylperoxy-2-ethylhexanoate, cumene hydroperoxide, t-butyl hydroperoxide, and 2,3-dimethyl-2,3-diphenylbutane.

Among these, according to the present invention, as the thermal radical polymerization initiator, it is preferable to use a hydroperoxide-based thermal radical polymerization initiator having a hydroperoxide group in a molecule and it is more preferable to use at least one hydroperoxide-based thermal radical polymerization initiator having a hydroperoxide group in a molecule and at least one non-hydroperoxide-based thermal radical polymerization initiator not having a hydroperoxide group in a molecule.

According to the present invention, PERBUTYL O (t-butylperoxy-2-ethylhexanoate) manufactured by NOF Corporation may be preferably used as the non-hydroperoxide-based thermal radical polymerization initiator, and PERCUMYL H-80 (cumene hydroperoxide) manufactured by NOF Corporation may be preferably used as the hydroperoxide-based thermal radical polymerization initiator.

As the preferable reason of using the hydroperoxide-based thermal radical polymerization initiator having a hydroperoxide group in a molecule as the thermal radical polymerization initiator, the hydroperoxide-based thermal radical polymerization initiator has an effect of promoting a chain transfer of the nonconjugated vinylidene group-containing compound monomer in the polymerization, the controllability of the three-dimensional structure is further improved, and the deformability of the semi-cured product may be provided. The hydroperoxide-based thermal radical polymerization initiator generally has a high temperature of initiating the thermal radical polymerization, and thus it is more preferable to use a non-hydroperoxide-based thermal radical polymerization initiator having a low thermal polymerization initiation temperature together.

The content of the thermal radical polymerization initiator is preferably 0.01 to 10 mass %, more preferably 0.05 to 5.0 mass %, and even more preferably 0.05 to 2.0 mass % with respect to the total mass of the curable composition.

The curable composition preferably includes both of the photoradical polymerization initiator and the thermal radical polymerization initiator. In this case, the total content of the photoradical polymerization initiator and the thermal radical polymerization initiator is preferably 0.01 to 10 mass %, more preferably 0.05 to 5.0 mass %, and even more preferably 0.05 to 3.0 mass % with respect to a total mass of a curable composition.

(Other Additives)

According to the present invention, without departing from the gist of the present invention, the curable composition may include additives such as polymers, other monomers, dispersing agents, plasticizers, heat stabilizers, and release agents.

(Method of Manufacturing Semi-Cured Product)

It is possible to manufacture a semi-cured product by semi-curing the curable composition of the present invention. The method of manufacturing a semi-cured product includes a step of semi-curing the curable composition of the present invention, and the semi-curing step may be a step of performing light irradiation or heating.

In the semi-curing step, at least one of the light irradiation or heating is performed on the curable composition of the present invention, it is preferable to form a semi-cured product in which the complex viscosity at 25° C. and a frequency of 10 Hz is $10^5$ to $10^8$ mPa·s.

Here, the "semi-cured product" in the present specification refers to a product that obtained by polymerizing the curable composition, that is not completely solid, and that has fluidity to some extent. In a case where the complex viscosity of the polymer of the curable composition at 25° C. and a frequency of 10 Hz is $10^5$ to $10^8$ mPa·s, this polymer is a semi-cured product. That is, a product in which the upper limit value of the complex viscosity at 25° C. and a frequency of 10 Hz is up to $1.0 \times 10^9$ mPa·s is considered as a semi-cured product. Meanwhile, the "cured product" refers to a product that is obtained by polymerizing the curable composition and that is in a complete solid state.

Hereinafter, a method of manufacturing the semi-cured product and a method of manufacturing a cured product are specifically described. Since the method of manufacturing the cured product includes a method of manufacturing a semi-cured product, a preferable aspect of a manufacturing method that is commonly applied to the both is described in a section of a method of manufacturing a semi-cured product.

<Semi-Curing Step>

The method of manufacturing a semi-cured product preferably includes a step of performing light irradiation and/or heating on a curable composition and obtaining a semi-cured product in which the complex viscosity at 25° C. and a frequency of 10 Hz is $10^5$ to $10^8$ mPa·s.

In the method of manufacturing a semi-cured product, the curable composition may be directly provided in a mold used in the thermal polymerization before the light irradiation and/or heating, or the curable composition may be put into another mold to manufacture a semi-cured product and moved to a mold used in a case of performing thermal polymerization.

In a case where another mold is used as the mold, it is preferable to use a so-called preform mold. The preform mold may be made of metal or may be made of glass or a resin. Considering repeated use in the mass production process, it is preferable that the preform mold is made of metal or glass. In a case where the semi-cured product is used as a lens, it is preferable that at least one surface of the preform mold has the same or similar shape as the mold and it is more preferable that both surfaces have the same or similar shape as the mold.

(Condition of Light Irradiation)

The light irradiation in the method of manufacturing a semi-cured product is performed such that the complex viscosity of the semi-cured product after the light irradiation at 25° C. and a frequency of 10 Hz is preferably $10^5$ to $10^8$ mPa·s, more preferably $10^5$ to $10^{7.5}$ mPa·s, and particularly preferably $10^{5.5}$ to $10^{7.5}$ mPa·s.

The light used in the light irradiation is preferably ultraviolet rays or visible light and more preferably ultraviolet rays. For example, a metal halide lamp, a low-pressure mercury lamp, a high-pressure mercury lamp, an extra-high pressure mercury lamp, a sterilization lamp, a xenon lamp, a light emitting diode (LED) light source lamp, and the like are suitably used. The atmosphere during light irradiation is preferably an atmosphere in the air or an atmosphere substituted with inert gas and more preferably an atmosphere substituted with nitrogen until the oxygen concentration becomes 1% or less.

(Condition of Heating and Semi-Curing)

In a case where a heating and semi-curing step is provided in the method of manufacturing a semi-cured product, the heating and semi-curing is performed such that the complex viscosity of the semi-cured product after heating at 25° C. and a frequency of 10 Hz is preferably $10^5$ to $10^8$ mPa·s, more preferably $10^5$ to $10^{7.5}$ mPa·s, and particularly preferably $10^{5.5}$ to $10^{7.5}$ mPa·s.

(Semi-Cured Product)

The present invention may relate to a semi-cured product manufactured by the above method. The semi-cured product is preferably used by the method of manufacturing a cured product described below. Here, the preferable range of the complex viscosity of the semi-cured product is the same as that of the complex viscosity of the semi-cured product by the method of manufacturing the semi-cured product.

All of the photoradical polymerization initiator is completely consumed in the semi-cured product after the light irradiation step, and the photoradical polymerization initiator may be retained.

The glass transition temperature (hereinafter, referred to as Tg) of the semi-cured product is preferably −150° C. to 0° C., more preferably −50° C. to 0° C., and particularly preferably −20° C. to 0° C.

(Method of Manufacturing Cured Product)

The method of manufacturing a cured product preferably includes a polymerization step of introducing a semi-cured product into a mold, subjecting the semi-cured product to pressure deformation, and performing photopolymerization by heating and thermal polymerization by light irradiation, so as to obtain a cured product.

The method of manufacturing a cured product preferably includes a step of performing at least one of the light irradiation and heating on the curable composition of the present invention, obtaining a semi-cured product in which the complex viscosity at 25° C. and a frequency of 10 Hz is $10^5$ to $10^8$ mPa·s and a polymerization step of introducing the semi-cured product in the mold, performing deformation under pressure, and performing at least one of light irradiation and heating, so as to obtain a cured product. The light irradiation condition and the heating condition in the step of manufacturing the cured product are the same as the conditions in the semi-curing step.

(Thermal Polymerization Step)

In a case where the step of manufacturing a cured product is a thermal polymerization step, the mold used in the polymerization step refers to a thermoforming mold. The thermoforming mold preferably has a configuration of combining two molds and heating a content under pressurization. In the method of manufacturing a cured product, it is more preferable to use a die as a mold in the thermal polymerization step of obtaining the cured product. As the thermoforming mold, for example, thermoforming molds disclosed in JP2009-126011A may be used.

(Introduction to Mold)

In the method of manufacturing a cured product, firstly, the manufactured semi-cured product is introduced to the mold by the method of manufacturing a semi-cured product. As described in the method of manufacturing of the semi-cured product, the semi-cured product after light irradiation and/or heating is directly provided in the thermoforming mold and subjected to the light irradiation and/or heating or is introduced to another mold different from the thermoforming mold and subjected to the light irradiation and/or heating. In a case where the semi-cured product after the light irradiation is directly provided in the thermoforming mold and subjected to the light irradiation and/or heating, particularly, the operation of performing introduction to the thermoforming mold is not necessary. In a case where the semi-cured product after the light irradiation and/or heating is introduced to another mold different from the thermoforming mold and subjected to the light irradiation and/or heating, it is preferable to include a step of moving the semi-cured product to a thermoforming mold. As the method of moving the semi-cured product after the light irradiation and/or heating to the thermoforming mold, for example, a syringe, an air tweezer having a vacuum pad and a vacuum generator, or the like may be used. The semi-cured product has the complex viscosity in the specific range, and thus is preferably moved easily to a thermoforming mold by using an air tweezer and the like.

(Deformation Under Pressure-Heating)

In the method of manufacturing a cured product, the semi-cured product introduced to the mold is deformed under pressure, heated, and thermally polymerized, so as to obtain a cured product. Here, the deformation under pressure and heating may be simultaneously performed, heating may be performed after deformation under pressure, and deformation under pressure may be performed after heating. However, it is preferable that the deformation under pressure and the heating are simultaneously performed. After the deformation under pressure and the heating are simultaneously performed, it is preferable to perform heating at a higher temperature after the pressurization is stabilized.

The pressure during the deformation under pressure is preferably 0.098 MPa to 9.8 MPa, more preferably 0.294 MPa to 4.9 MPa, and particularly preferably 0.294 MPa to 2.94 MPa. The heating temperature of the heating simultaneously performed with deformation under pressure is preferably 80° C. to 300° C., more preferably 120° C. to 300° C., and particularly preferably 150° C. to 280° C. In a case of the heating at a higher temperature after the pressurization is stabilized, the heating temperature is preferably 80° C. to 300° C., more preferably 120° C. to 300° C., and particularly preferably 150° C. to 280° C. The time of the thermal polymerization is preferably 30 to 1,000 seconds, more preferably 30 to 500 seconds, and particularly preferably 60 to 300 seconds. The atmosphere during thermal polymerization is preferably an atmosphere in the air or an atmosphere substituted with inert gas and more preferably an atmosphere substituted with nitrogen until the oxygen concentration becomes 1% or less.

(Cured Product)

The present invention also relates to a cured product of the curable composition. The cured product is formed by curing the curing components. The cured product of the present invention is preferably manufactured by the method of manufacturing the cured product.

(Refractive Index)

Among applications as an optical member, in view of being used as a lens, the cured product of the present invention preferably has a high refractive index. A refractive index nD of the cured product of the present invention at a wavelength of 589 nm is preferably 1.45 or more, more preferably 1.58 or more, particularly preferably 1.60 or more, particularly preferably 1.61 or more, and most preferably 1.62 or more.

(Abbe Number)

The cured product of the present invention preferably has a low Abbe number, in view of decreasing the chromatic aberration in a case of being used as a lens or the like among applications as an optical member. The Abbe number of the cured product of the present invention is preferably 24 or less, more preferably 23.5 or less, and particularly preferably 22 or less.

In the present specification, an Abbe refractometer (manufactured by Kalnew Optical Industrial Co., Ltd.) is used, the refractive indexes nD, nF, and nC at wavelengths 589 nm, 486 nm, and 656 nm are measured, and the Abbe number (νD) is calculated by the following equation.

$$\nu D = (nD-1)/(nF-nC)$$

Here, nD represents a refractive index at a wavelength of 589 nm, nF represents a refractive index at a wavelength of 486 nm, and nC represents a refractive index at a wavelength of 656 nm.

(Abnormal Dispersibility)

With respect to the cured product of the present invention, it is preferable that an abnormal dispersibility is high. The abnormal dispersibility of the cured product of the present invention is preferably 0.55 or more, more preferably 0.60 or more, and even more preferably 0.63 or more.

In the present specification, an Abbe refractometer (manufactured by Kalnew Optical Industrial Co., Ltd.) is used, the refractive indexes nD, nF, nC, and ng at wavelengths of 589 nm, 486 nm, 656 nm, and 435.8 nm are measured, and the abnormal dispersibility (θg, F) is calculated by the following equation.

$$\theta g, F = (ng-nF)/(nF-nC)$$

Here, nD represents a refractive index at a wavelength of 589 nm, nF represents a refractive index at a wavelength of 486 nm, nC represents a refractive index at a wavelength of 656 nm, and ng represents a refractive index at a wavelength of 435.8 nm.

(Size)

The maximum thickness of the cured product of the present invention is preferably 0.1 to 10 mm. The maximum thickness is more preferably 0.1 to 5 mm and particularly preferably 0.15 to 3 mm. The maximum diameter of the cured product of the present invention is preferably 1 to 1,000 mm. The maximum diameter is more preferably 2 to 200 mm and particularly preferably 2.5 to 100 mm. The cured product of this size is particularly useful as the application as an optical member having a high refractive index. Even in a case where such a thick molded article is manufactured by the solution casting method, since it is difficult to remove the solvent, generally the manufacturing is not easy, and also molding is not easy. However, in a case where the curable composition of the present invention is used, it is possible to obtain a cured product that is easily molded, that has high handleability, and has a high quality.

(Optical Member)

The present invention also relates to an optical member including a cured product. The cured product of the present invention is a molded article having excellent optical properties, and thus is preferably used in an optical member. The types of the optical member of the present invention are particularly limited. Particularly, an optical member using the excellent optical properties of the curable composition may be suitably used as an optical member (so-called passive optical member) that transmits light. Examples of the optical functional device having such an optical member include various display devices (liquid crystal display, plasma display, and the like), various projector devices (overhead projector (OHP), liquid crystal projector, and the like), an optical fiber communication device (optical waveguide, an optical amplifier, and the like), and a photographing device such as cameras and video.

Examples of the passive optical member used in the optical functional device include a lens, a prism, a prism sheet, a panel (plate-like molded article), a film, an optical waveguide (having a film shape, a fiber shape, or the like), an optical disc, and a sealing agent of LED. Such a passive optical member may be provided with any coating layer, if necessary, for example, a protective layer for preventing mechanical damage of the coated surface due to friction or abrasion, a light absorbing layer for absorbing rays having undesirable wavelengths causing deterioration of inorganic particles, a substrate, or the like, a transmission shielding layer for suppressing or preventing permeation of reactive low molecules such as moisture and oxygen gas, an antiglare layer, an antireflection layer, a layer of a low refractive index, and any additional functional layers may be provided. Specific examples of any coating layer include a transparent conductive film including an inorganic oxide coating layer, a gas barrier film, a gas barrier film including an organic coating layer, or a hard coat. As a coating method, known coating methods such as a vacuum deposition method, a chemical vapor deposition (CVD) method, a sputtering method, a dip coating method, and a spin coating method may be used.

Application Example

The optical member using the cured product of the present invention is preferably used particularly in a lens substrate. The lens substrate manufactured by using the curable composition of the present invention has the low Abbe number, preferably has a high refractive index, light transmittance, and light weight, and has excellent optical properties. It is possible to optionally adjust the refractive index of the lens substrate by suitably adjusting the types of the monomer for forming the curable composition.

In the present specification, a "lens substrate" means a single member that may exhibit a lens function. A film or a member may be provided on the surface or the periphery of the lens substrate according to the use environment and application of the lens. For example, a protective film, an antireflection film, a hard coat film, and the like may be formed on the surface of the lens substrate. A composite lens obtained by laminating a glass lens substrate or a plastic lens substrate may be provided. The periphery of the lens substrate may be fitted and fixed in the substrate holding frame or the like. However, these films, frames, and the like are members to be added to the lens substrate and are distinguished from the lens substrate in the present specification.

In a case where the lens substrate is used as a lens, the lens substrate may be used as a lens alone, or the film, a frame, another lens substrate, and the like may be added to be used as a lens. The types and the shapes of the lens using the lens substrate are not particularly limited.

The lens substrate has the low Abbe number, and thus may be preferably used in a chromatic aberration correcting lens, and the chromatic aberration correcting lens, for example, is preferably used for an image pickup lens of mobile phones, digital cameras, and the like, a photographing lens of televisions, video cameras, and the like, an in-vehicle lens, and an endoscope lens.

EXAMPLES

Hereinafter, characteristics of the present invention are more specifically described with reference to the examples and comparative examples. A material, an amount used, a treatment detail, a treatment order, and the like provided in the following examples can be suitably changed without departing from the gist of the present invention. Accordingly, the scope of the present invention should not be construed in a limited manner by the following specific examples.

Synthesis of Compound A 132 mL of triethylamine and 650 mL of butyl acetate were added to 100 g of 2-hydroxyethyl acrylate and stirred. While the reaction solution was maintained at 5° C., 70 mL of methanesulfonic acid chloride was added dropwise over one hour. After stirring was performed for one hour, 500 mL of water was added to the reaction solution and stirred, and an operation of removing a water layer was repeated three times. After 30 mg of dibutylhydroxytoluene was added, butyl acetate was distilled off under reduced pressure, so as to obtain 160 g of Compound A.

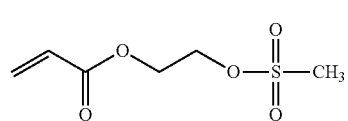

Compound A

Synthesis of Precursor 4

50 mL of ethanol and 10 mL of acetic acid were added to 21.6 g of o-phenylenediamine and 35.6 g of ninhydrin, and reaction was performed at 70° C. for three hours. After the reaction solution was cooled to room temperature, the precipitated crystals were collected by filtration, washed with ethanol, and dried to obtain 40.9 g of Precursor 4. Precursor 4

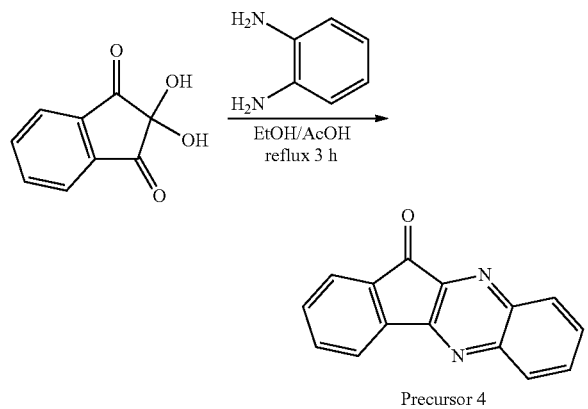

Precursor 4

Synthesis of Compound (4)

20 g of Precursor 4 and 32 g of phenol were dissolved in 30 mL of methanesulfonic acid. The reaction solution was warmed and maintained at 100° C., and 0.3 mL of 3-mercaptopropionic acid was dropwise added. After stirring was performed for three hours, 70 mL of toluene was dropwise added to the reaction solution and was stirring for 30 minutes, and 140 mL of toluene was further added dropwise. The reaction solution was returned to room temperature, and the precipitated crystals were collected by filtration so as to obtain 29 g of Compound (4). $^1$H-NMR data of Compound (4) was as follows.

$^1$H-NMR (300 MHz, DMSO (Dimethyl sulfoxide)-d6): δ6.60-6.70 ppm (d, 4H), 6.95-7.05 ppm (d, 4H), 7.55-7.70 ppm (m, 3H), 7.75-7.90 ppm (m, 2H), 8.00-8.10 ppm (d, 1H), 8.12-8.22 ppm (m, 2H), 9.40 ppm (bs, 2H)

Synthesis of Compound (24)

50 mL of tetrahydrofuran, 0.05 mL of nitrobenzene, 13.8 g of potassium carbonate, and 0.8 g of tetrabutylammonium bromide (TBAB) were added to 10 g of Compound (4), and stirred. 15 g of compound A was added to the reaction solution, reaction was performed for five hours while the temperature was maintained at 80° C., 100 mL of toluene was added, and stirring was performed. 100 mL of water was added to the reaction solution, stirring was performed while the temperature was maintained at 60° C., and an operation of removing a water layer was repeated three times. The residue was purified by silica gel column chromatography so as to obtain 12 g of Compound (24). $^1$H-NMR data of Compound (24) was as follows.

$^1$H-NMR (300 MHz, DMSO-d6): δ4.10-4.20 ppm (m, 4H), 4.35-4.45 ppm (m, 4H), 5.85-5.95 ppm (m, 1H), 6.15-6.25 ppm (m, 1H), 6.30-6.40 ppm (m, 1H), 6.85-6.95 ppm (d, 4H), 7.05-7.15 ppm (d, 4H), 7.55-7.70 ppm (m, 3H), 7.75-7.90 ppm (m, 2H), 8.00-8.10 ppm (d, 1H), 8.15-8.25 ppm (m, 2H)

Synthesis of Compound (49)

Compound (49) was synthesized in the same manner as in the synthesis of compound (4), except for changing phenol to 2,6-dimethylphenol. $^1$H-NMR data of Compound (49) was as follows.

$^1$H-NMR (300 MHz, DMSO-d6): δ2.10 ppm (s, 12H), 6.70 ppm (bs, 2H), 6.80 ppm (s, 4H), 7.55-7.70 ppm (m, 3H), 7.75-7.90 ppm (m, 2H), 8.00-8.10 ppm (d, 1H), 8.12-8.22 ppm (m, 2H)

Synthesis of Compound (51)

Compound (51) was synthesized in the same manner as in the synthesis of compound (24), except for changing Compound (4) to Compound (49). $^1$H-NMR data of Compound (51) was as follows.

$^1$H-NMR (300 MHz, DMSO-d6): δ2.10 ppm (s, 12H), 3.95-4.05 ppm (m, 4H), 4.35-4.45 ppm (m, 4H), 5.90-6.00 ppm (m, 1H), 6.15-6.25 ppm (m, 1H), 6.30-6.40 ppm (m, 1H), 6.85-6.95 ppm (s, 4H), 7.60-7.70 ppm (m, 3H), 7.75-7.90 ppm (m, 2H), 8.00-8.10 ppm (d, 1H), 8.15-8.25 ppm (m, 2H)

Synthesis of Precursor 7

Precursor 7 was synthesized by the method disclosed in RSC Advances 4 (2014), p 37806.

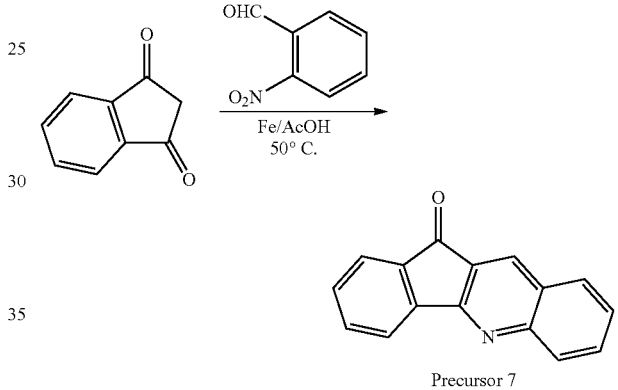

Precursor 7

Synthesis of Compound (7)

Compound (7) was synthesized in the same manner as in the synthesis of compound (4), except for changing Precursor 4 to Precursor 7. $^1$H-NMR data of Compound (7) was as follows.

$^1$H-NMR (300 MHz, DMSO-d6): δ6.60-6.70 ppm (d, 4H), 6.95-7.05 ppm (d, 4H), 7.55-7.70 ppm (m, 4H), 7.80-7.90 ppm (m, 1H), 8.05-8.10 ppm (d, 1H), 8.15-8.20 ppm (d, 1H), 8.20-8.25 ppm (d, 1H), 8.50 ppm (s, 1H)

Synthesis of Compound (27)

Compound (27) was synthesized in the same manner as in the synthesis of compound (24), except for changing Compound (4) to Compound (7). $^1$H-NMR data of Compound (27) was as follows.

$^1$H-NMR (300 MHz, DMSO-d6): δ4.05-4.15 ppm (m, 4H), 4.35-4.45 ppm (m, 4H), 5.85-5.95 ppm (m, 1H), 6.15-6.25 ppm (m, 1H), 6.30-6.40 ppm (m, 1H), 6.85-6.95 ppm (d, 4H), 7.05-7.15 ppm (d, 4H), 7.55-7.70 ppm (m, 4H), 7.80-7.90 ppm (m, 1H), 8.05-8.10 ppm (d, 1H), 8.15-8.20 ppm (d, 1H), 8.20-8.25 ppm (d, 1H), 8.50 ppm (s, 1H)

Synthesis of Precursor 16

Precursor 16 was synthesized by the method disclosed in paragraph 0116 of JP5249781B.

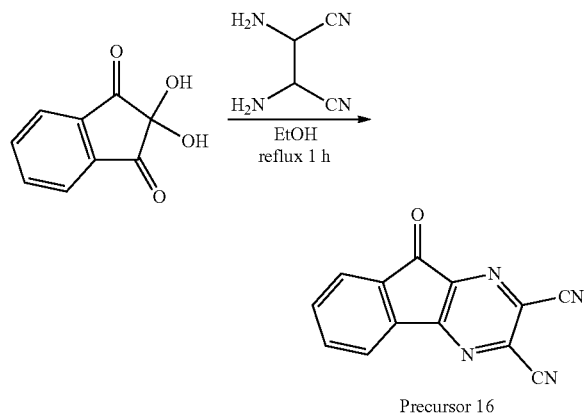

Precursor 16

Synthesis of Compound (16)

Compound (16) was synthesized in the same manner as in the synthesis of compound (4), except for changing Precursor 4 to Precursor 16. ¹H-NMR data of Compound (16) was as follows.

¹H-NMR (300 MHz, DMSO-d6): δ6.60-6.70 ppm (d, 4H), 6.85-6.95 ppm (d, 4H), 7.60-7.80 ppm (m, 3H), 8.20 ppm (d, 1H), 9.6 ppm (s, 2H)

Synthesis of Compound (36)

Compound (36) was synthesized in the same manner as in the synthesis of compound (24), except for changing Compound (4) to Compound (16). ¹H-NMR data of Compound (36) was as follows.

¹H-NMR (300 MHz, DMSO-d6): δ4.00-4.10 ppm (m, 4H), 4.30-4.40 ppm (m, 4H), 5.85-5.95 ppm (m, 1H), 6.15-6.25 ppm (m, 1H), 6.30-6.40 ppm (m, 1H), 6.80-6.90 ppm (d, 4H), 7.00-7.10 ppm (d, 4H), 7.60-7.80 ppm (m, 3H), 8.20 ppm (d, 1H)

Synthesis of Compound (54)

50 ml of methanesulfonic acid was slowly added dropwise to a slurry solution of 10 g of precursor 16, 25 ml of 2,6-dimethylaniline, and 75 ml of dimethyl carbonate. After stirring was performed at 60° C. for two hours, the temperature of the reaction system was raised to 100° C. The reaction was performed for two hours while refluxing dimethyl carbonate was distilled off, the temperature of the reaction system was cooled to room temperature, and ethyl acetate was added, so to dilute the organic layer. The reaction system was neutralized with potassium carbonate aqueous solution, and the solution separation was performed twice with saline. The organic layer was concentrated and purified by silica gel chromatography to obtain 10.3 g of Compound (54). ¹H-NMR data of Compound (54) was as follows.

¹H-NMR (300 MHz, CDCl₃): δ2.10 (s, 12H), 3.60 (bs, 4H), 6.70 (s, 4H), 7.50-7.65 (m, 3H), 8.15 (d, 1H)

Synthesis of Precursor 9

Precursor 9 was synthesized in the same manner as in the synthesis of Precursor 4, except for changing o-phenylenediamine to 2,3-diaminopyridine.

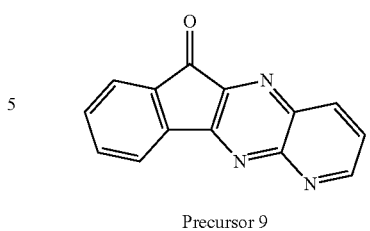

Precursor 9

Synthesis of Compound (9)

Compound (9) was synthesized in the same manner as in the synthesis of compound (4), except for changing Precursor 4 to Precursor 9. ¹H-NMR data of Compound (9) was as follows.

¹H-NMR (300 MHz, DMSO-d6): δ6.60-6.70 ppm (d, 4H), 6.95-7.05 ppm (d, 4H), 7.55-7.70 ppm (m, 3H), 7.75-7.85 ppm (m, 1H), 8.22-8.28 ppm (d, 1H), 8.45-8.55 ppm (d, 1H), 9.05-9.15 ppm (m, 1H), 9.35-9.50 ppm (bs, 2H)

Synthesis of Compound (29)

Compound (29) was synthesized in the same manner as in the synthesis of compound (24), except for changing Compound (4) to Compound (9). ¹H-NMR data of Compound (29) was as follows.

¹H-NMR (300 MHz, DMSO-d6): δ4.10-4.20 ppm (m, 4H), 4.35-4.45 ppm (m, 4H), 5.85-5.95 ppm (m, 1H), 6.15-6.25 ppm (m, 1H), 6.30-6.40 ppm (m, 1H), 6.85-6.95 ppm (d, 4H), 7.05-7.15 ppm (d, 4H), 7.55-7.70 ppm (m, 3H), 7.75-7.85 ppm (m, 1H), 8.15-8.20 ppm (d, 1H), 8.45-8.55 ppm (d, 1H), 9.05-9.15 ppm (m, 1H)

Synthesis of Compound (60)

Compound (60) was synthesized in the same manner as in the synthesis of compound (24), except for changing Compound A to p-toluenesulfonic acid (2R)-(−)-glycidyl (manufactured by Tokyo Chemical Industry Co., Ltd.)¹H-NMR data of Compound (60) was as follows.

¹H-NMR (300 MHz, DMSO-d6): δ2.63-2.67 ppm (dd, 2H), 2.85 ppm (t, 2H), 3.70-3.75 ppm (dd, 2H), 4.20-4.25 ppm (dd, 2H, 6.85-6.95 ppm (d, 4H), 7.05-7.15 ppm (d, 4H), 7.54-7.70 ppm (m, 3H), 7.75-7.90 ppm (m, 2H), 8.00-8.10 ppm (d, 1H), 8.15-8.25 ppm (m, 2H)

<Comparative Compound>

As comparative compounds, the following compounds were used.

Comparative Compound 1-1

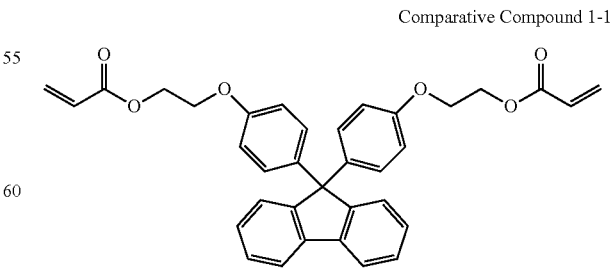

As Comparative Compound 1-1, trade name "OGSOL EA-0200" manufactured by Osaka Gas Chemicals Co., Ltd. was used.

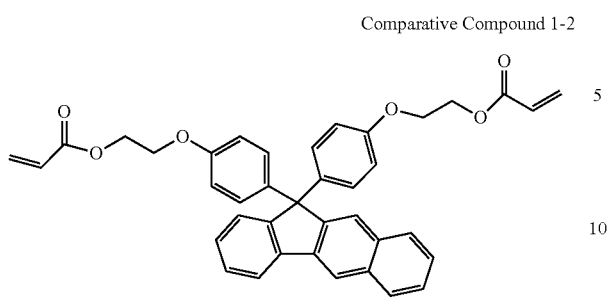

Comparative Compound 1-2

Comparative Compound 1-2 was synthesized by a synthesis method disclosed in Example 1 of JP2014-80572A.

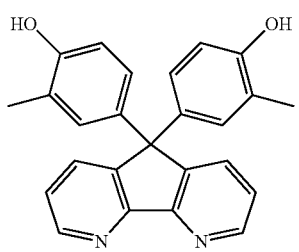

Comparative Compound 1-3

Comparative Compound 1-3 was synthesized by a synthesis method disclosed in paragraph 0140 of JP2009-234999A.

Examples 1 to 12 and Comparative Examples 1 to 3

The above compound and the following components were added such that the composition presented in Table 2 was obtained and stirred to be uniform, so as to prepare a curable composition.

<(Meth)Acrylate Monomer>

As the (meth)acrylate monomers, the following compounds were used.

Monomer 1: Trade name: VISCOAT #192 PEA manufactured by Osaka Organic Chemical Industry Ltd.

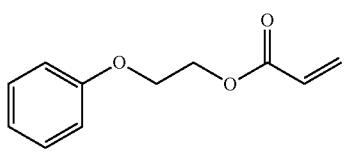

Monomer 1

<Nonconjugated Vinylidene Group-Containing Compound>

As the nonconjugated vinylidene group-containing compound, the following compound (β-caryophyllene manufactured by Inoue Perfumery Mfg. Co., Ltd.) was used. The optical isomers do not have to be particularly limited.

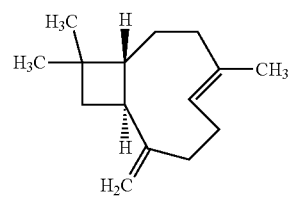

<Photoradical Polymerization Initiator>

As the photoradical polymerization initiator, the following compound (Irgacure 819 manufactured by BASF SE) was used.

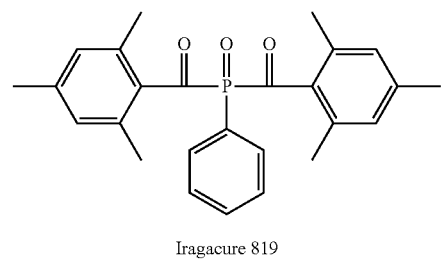

Iragacure 819

<Thermal Radical Polymerization Initiator>

As the thermal radical polymerization initiator, the following compound was used.

PERBUTYL O: manufactured by NOF Corporation
PERCUMYL H-80: manufactured by NOF Corporation

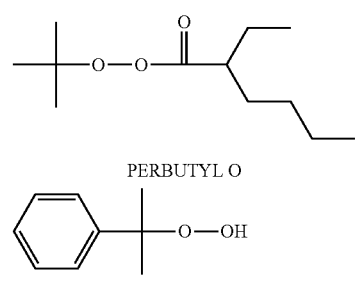

PERBUTYL O

PERCUMYL H-80

(Evaluation)
<Abbe Number and Abnormal Dispersibility>

The curable compositions obtained in the examples and the comparative examples were introduced to a transparent glass mold having a diameter of 10 mm and a thickness of 1 mm and were heated to 200° C. in the atmosphere in which the oxygen concentration of 1% or less, so as to manufacture thermally cured products. The Abbe number (vD) and the abnormal dispersibility (θg, F) of the obtained thermally cured product were measured by using the Abbe refractometer (manufactured by Kalnew Optical Industrial Co., Ltd.).

$$vD=(nD-1)/(nF-nC)$$

$$\theta g, F=(ng-nF)/(nF-nC)$$

Here, nD represents a refractive index at a wavelength of 589 nm, nF represents a refractive index at a wavelength of 486 nm, nC represents a refractive index at a wavelength of 656 nm, and ng represents a refractive index at a wavelength of 435.8 nm.

In this measurement, thermally cured products were used, but there was no change in the Abbe number, even in a case of a cured product obtained by thermally curing after the irradiation with ultraviolet rays.

<Surface Transferability>

200 mg of the curable composition was introduced into a molding die whose surface was treated with chromium nitride, a transparent glass lens (Convex lens having glass material=BK7, diameter of 33 mm, center thickness of 3 mm, radius of curvature of the surface in contact with the curable composition=44.3 mm, radius of curvature of the surface not in contact with the curable composition=330.9 mm) was placed so as to cover all the surfaces of the curable composition which is not in contact with the molding die, and the curable composition was expanded to have a diameter of 30 mm. After this state was obtained, the upper side of the glass lens using Execure 3000 (manufactured by HOYA Corporation) was irradiated with ultraviolet rays of 300 mJ/cm$^2$, and while the state of being sandwiched between the molding die and the glass lens was maintained, a pressure of 0.196 MPa (2 kgf/cm$^2$) was applied to the curable composition and the temperature was raised to 200° C. Thereafter, a composite lens was manufactured by separating the cured product of the curable composition and the molding die at a speed of 0.05 mm/sec.

Ten composite lenses for evaluating surface transferability were manufactured by repeating the above operation 10 times. The external appearance of the manufactured composite lens was evaluated by using a digital microscope (trade name: VHX-1000) manufactured by Keyence Corporation. A cured product having fine irregularities (wrinkles) on the surface of the composite lens was determined as a defective product, and a cured product not having fine irregularities (wrinkles) was determined as a non-defective product. Ten composite lenses were evaluated, and a proportion of non-defective products out of the composite lenses was set as a non-defective rate and was evaluated according to the following standard.

A: A non-defective rate was 90% or more.
B: A non-defective rate was 50% or more and less than 90%.
C: A non-defective rate was less than 50%.

TABLE 2

|  |  | Example 1 | Example 2 | Example 3 | Example 4 | Example 5 | Example 6 | Example 7 | Example 8 | Example 9 |
|---|---|---|---|---|---|---|---|---|---|---|
| Compound | Compound (24) | 45.9 |  |  |  |  |  |  |  |  |
|  | Compound (51) |  | 45.9 | 51.9 | 60.9 | 45.9 |  |  |  |  |
|  | Compound (27) |  |  |  |  |  | 60.9 |  |  |  |
|  | Compound (29) |  |  |  |  |  |  | 45.9 |  |  |
|  | Compound (36) |  |  |  |  |  |  |  | 60.9 | 45.9 |
|  | Compound (49) |  |  |  |  | 15 |  |  |  |  |
|  | Compound (54) |  |  |  |  |  |  |  |  | 15 |
|  | Compound (60) |  |  |  |  |  |  |  |  |  |
|  | Compound (4) |  |  |  |  |  |  |  |  |  |
| Comparative Compound | Comparative Compound 1-1 |  |  |  |  |  |  |  |  |  |
|  | Comparative Compound 1-2 |  |  |  |  |  |  |  |  |  |
|  | Comparative Compound 1-3 |  |  |  |  |  |  |  |  |  |
| (Meth)acrylate monomer | Monomer 1 | 47.8 | 47.8 | 41.8 | 32.8 | 32.8 | 32.8 | 47.8 | 32.8 | 32.8 |
| Nonconjugated vinylidene group-containing compound | β-caryophyllene | 4.5 | 4.5 | 4.5 | 4.5 | 4.5 | 4.5 | 4.5 | 4.5 | 4.5 |
| Photoradical polymerization initiator | Irgacure819 | 0.1 | 0.1 | 0.1 | 0.1 | 0.1 | 0.1 | 0.1 | 0.1 | 0.1 |
| Thermal radical polymerization initiator | PERBUTYL O | 1.0 | 1.0 | 1.0 | 1 | 1 | 1 | 1 | 1 | 1 |
|  | PERCUMYL H-80 | 0.7 | 0.7 | 0.7 | 0.7 | 0.7 | 0.7 | 0.7 | 0.7 | 0.7 |
| Curable compound | vD | 23.8 | 24.0 | 23.0 | 21.4 | 21.5 | 21.5 | 21.9 | 21.6 | 21.3 |
|  | θg, F | 0.605 | 0.601 | 0.639 | 0.701 | 0.698 | 0.603 | 0.652 | 0.649 | 0.655 |
| Composite lens evaluation | Surface transferability | B | B | A | A | B | A | B | A | B |

|  |  | Example 10 | Example 11 | Example 12 | Comparative Example 1 | Comparative Example 2 | Comparative Example 3 |
|---|---|---|---|---|---|---|---|
| Compound | Compound (24) |  |  |  |  |  |  |
|  | Compound (51) |  |  | 45.9 |  |  |  |
|  | Compound (27) |  |  |  |  |  |  |
|  | Compound (29) |  |  |  |  |  |  |
|  | Compound (36) |  |  |  |  |  |  |
|  | Compound (49) | 51.9 |  |  |  |  |  |
|  | Compound (54) |  |  |  |  |  |  |
|  | Compound (60) |  | 51.9 |  |  |  |  |
|  | Compound (4) |  |  | 15 |  |  |  |
| Comparative Compound | Comparative Compound 1-1 |  |  |  | 60.9 |  | 45.9 |
|  | Comparative Compound 1-2 |  |  |  |  | 60.9 |  |
|  | Comparative Compound 1-3 |  |  |  |  |  | 15 |

TABLE 2-continued

| | | | | | | | |
|---|---|---|---|---|---|---|---|
| (Meth)acrylate monomer | Monomer 1 | 41.8 | 41.8 | 32.8 | 32.8 | 32.8 | 32.8 |
| Nonconjugated vinylidene group-containing compound | β-caryophyllene | 4.5 | 4.5 | 4.5 | 4.5 | 4.5 | 4.5 |
| Photoradical polymerization initiator | Irgacure819 | 0.1 | 0.1 | 0.1 | 0.1 | 0.1 | 0.1 |
| Thermal radical polymerization initiator | PERBUTYL O PERCUMYL H-80 | 1.0 0.7 | 1.0 0.7 | 1.0 0.7 | 1 0.7 | 1 0.7 | 1 0.7 |
| Curable compound | νD θg, F | 22.9 0.642 | 23.3 0.620 | 21.3 0.704 | 25.5 0.475 | 23.8 0.545 | 25.1 0.505 |
| Composite lens evaluation | Surface transferability | B | B | B | A | A | B |

From Table 2, it is known that the Abbe number of the cured product manufactured by using the curable composition including the compound of the present invention was low, and a high abnormal dispersibility was exhibited. Meanwhile, in the cured product manufactured by using the curable composition including the comparative compound, the low Abbe number and the high abnormal dispersibility were not compatible with each other.

From the results of Examples 3, 4, 6, and 8, in a case where $R^1$ and $R^2$ in Formula (1) include acrylate structures and in a case where the compound includes 50 mass % or more with respect to the total mass of the curable composition, surface transferability was particularly satisfactory.

What is claimed is:

1. A compound represented by Formula (1),

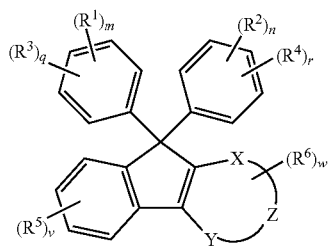

Formula (1)

in Formula (1), X and Y each independently represents an oxygen atom, a sulfur atom, a nitrogen atom, or a carbon atom, at least one of X or Y is an oxygen atom, a sulfur atom, or a nitrogen atom;

Z is an atomic group that forms a 5 to 7-membered ring together with X—C═C—Y and represents an atomic group including at least one selected from a carbon atom and a heteroatom;

$R^1$ and $R^2$ each independently represents a hydroxyl group, an alkoxy group having 2 to 6 carbon atoms that may have a substituent, a mercapto group, a thioalkoxy group having 2 to 6 carbon atoms that may have a substituent, an amino group, an alkylamino group having 1 to 6 carbon atoms that may have a substituent, a carboxy group, an alkylcarbonyloxy group having 1 to 6 carbon atoms that may have a substituent, a carbamoyloxy group that may have a substituent, or an alkoxycarbonyloxy group having 2 to 6 carbon atoms that may have a substituent;

$R^3$ to $R^5$ each independently represents a halogen atom, a halogenated alkyl group, an alkyl group, an alkenyl group, an acyl group, a hydroxyl group, a hydroxyalkyl group, an alkoxy group, an aryl group, a heteroaryl group, an alicyclic group, or a cyano group;

$R^6$ represents a halogen atom, a halogenated alkyl group, an alkyl group, an alkenyl group, an acyl group, a hydroxyl group, a hydroxyalkyl group, an alkoxy group, an aryl group, a heteroaryl group, an alicyclic group, or a cyano group;

m and n each independently represents an integer of 1 to 5, q and r each independently represents an integer of 0 to 4; here, 1≤m+q≤5, and 1≤n+r≤5 are satisfied;

v is an integer of 0 to 4, w is an integer of 0 or more, the maximum number of w is the maximum number of substituents that may be substituted with a ring formed by X—C═C—Y and Z;

in a case where q is an integer of 2 to 4, the plurality of $R^3$'s may be identical to or different from each other, and the plurality of $R^3$'s may be bonded to each other to form a ring;

in a case where r is an integer of 2 to 4, the plurality of $R^4$'s may be identical to or different from each other, and the plurality of $R^4$'s may be bonded to each other to form a ring;

in a case where v is an integer of 2 to 4, the plurality of $R^5$'s may be identical to or different from each other, but the plurality of $R^5$'s are not bonded to each other to form a ring; and in a case where w is an integer of 2 to 5, the plurality of $R^6$'s may be identical to or different from each other, and the plurality of $R^6$'s may be bonded to each other to form a ring, provided that in a case where a plurality of $R^6$'s are bonded to each other and are groups for forming a fused ring together with a substituted ring, the number of rings for forming a fused ring is 2.

2. The compound according to claim 1, wherein in Formula (1), $R^1$ and $R^2$ each independently represents a group having a hydroxyl group, a mercapto group, an amino group, a polymerizable unsaturated bond, an epoxy group, or an oxetanyl group.

3. The compound according to claim 1, wherein in Formula (1), $R^1$ and $R^2$ each independently represents a group represented by Formula (2);

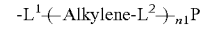

Formula (2)

in Formula (2), $L^1$ represents —O—, —S—, or —NH—, Alkylene represents an alkylene group having 2 to 6 carbon atoms, $L^2$ represents —O—, —S—, or —NH—, n1 represents an integer of 0 to 2, P is a hydrogen atom or a group represented by any one of Formulae (P1) to (P4); and

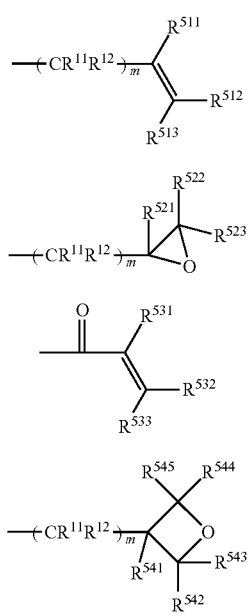

Formula (P1)

Formula (P2)

Formula (P3)

Formula (P4)

in Formulae (P) to (P4), $R^{511}$, $R^{512}$, $R^{513}$, $R^{521}$, $R^{522}$, $R^{523}$, $R^{531}$, $R^{532}$, $R^{533}$, $R^{541}$, $R^{542}$, $R^{543}$, $R^{544}$, and $R^{545}$ each independently represents a hydrogen atom or an alkyl group, m represents an integer of 0 to 2, and $R^{11}$ and $R^{12}$ each independently represents a hydrogen atom, a halogen atom, a halogenated alkyl group, an alkyl group, an alkenyl group, an acyl group, a hydroxyl group, a hydroxyalkyl group, an alkoxy group, an aryl group, a heteroaryl group, an alicyclic group, a cyano group, an epoxy group, an oxetanyl group, a mercapto group, an amino group, or a (meth) acryloyl group.

4. The compound according to claim 1,
wherein, in Formula (1), at least one selected from X and Y is a nitrogen atom.

5. The compound according to claim 1,
wherein, in Formula (1), $R^1$ and $R^2$ are the same group.

6. The compound according to claim 1, which is represented by Formula (3);

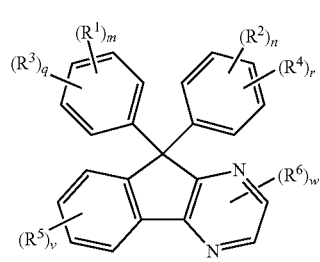

Formula (3)

in Formula (3), $R^1$ and $R^2$ each independently represents a hydroxyl group, an alkoxy group having 2 to 6 carbon atoms that may have a substituent, a mercapto group, a thioalkoxy group having 2 to 6 carbon atoms that may have a substituent, an amino group, an alkylamino group having 1 to 6 carbon atoms that may have a substituent, a carboxy group, an alkylcarbonyloxy group having 1 to 6 carbon atoms that may have a substituent, a carbamoyloxy group that may have a substituent, or an alkoxycarbonyloxy group having 2 to 6 carbon atoms that may have a substituent;

$R^3$ to $R^5$ each independently represents a halogen atom, a halogenated alkyl group, an alkyl group, an alkenyl group, an acyl group, a hydroxyl group, a hydroxyalkyl group, an alkoxy group, an aryl group, a heteroaryl group, an alicyclic group, or a cyano group;

$R^6$ represents a halogen atom, a halogenated alkyl group, an alkyl group, an alkenyl group, an acyl group, a hydroxyl group, a hydroxyalkyl group, an alkoxy group, an aryl group, a heteroaryl group, an alicyclic group, or a cyano group;

m and n each independently represents an integer of 1 to 5, q and r each independently represents an integer of 0 to 4; here, 1≤m+q≤5, and 1≤n+r≤5 are satisfied;

v is an integer of 0 to 4, and w is an integer of 0 to 2;

in a case where q is an integer of 2 to 4, the plurality of $R^3$'s may be identical to or different from each other, and the plurality of $R^3$'s may be bonded to each other to form a ring;

in a case where r is an integer of 2 to 4, the plurality of $R^4$'s may be identical to or different from each other, and the plurality of $R^4$'s may be bonded to each other to form a ring;

in a case where v is an integer of 2 to 4, the plurality of $R^5$'s may be identical to or different from each other, but the plurality of $R^5$'s are not bonded to each other to form a ring; and in a case where w is 2, the plurality of $R^6$'s may be identical to or different from each other, and the plurality of $R^6$'s may be bonded to each other to form a ring, provided that in a case where a plurality of $R^6$'s are bonded to each other and are groups for forming a fused ring together with a substituted ring, the number of rings for forming a fused ring is 2.

7. The compound according to claim 1,
wherein $R^1$ and $R^2$ are each independently represented by Formula (4);

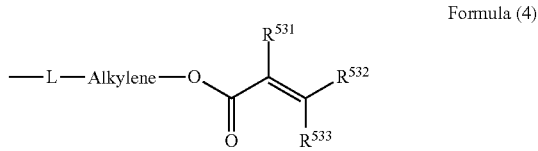

Formula (4)

in Formula (4), L represents —O—, —S—, or —NH—, Alkylene represents an alkylene group having 2 to 6 carbon atoms, and $R^{531}$, $R^{532}$, and $R^{533}$ each independently represents a hydrogen atom or an alkyl group.

8. A curable composition comprising the compound according to claim 1.

9. The curable composition according to claim 8,
wherein the curable composition contains a (meth)acrylate monomer and at least one selected from a photo-radical polymerization initiator and a thermal radical polymerization initiator.

10. The curable composition according to claim 9,
wherein viscosity of the (meth)acrylate monomer of the curable composition at 25° C. is less than 2,000 mPa·s.

11. A cured product of the curable composition according to claim 8.

12. An optical member comprising the cured product according to claim 11.

13. A lens comprising the cured product according to claim 11.

14. The compound according to claim 1,
wherein, in Formula (1), $R^3$ to $R^6$ each independently represents a halogen atom, an alkyl group, an alkoxy group, an aryl group, or a cyano group.

15. The compound according to claim 3, wherein, in Formulae (P1) to (P4), $R^{11}$ and $R^{12}$ each independently represents a hydrogen atom or an alkyl group.

* * * * *